(12) United States Patent
Qasba et al.

(10) Patent No.: US 7,482,133 B2
(45) Date of Patent: Jan. 27, 2009

(54) CATALYTIC DOMAINS OF β(1,4)-GALACTOSYLTRANSFERASE I HAVING ALTERED DONOR AND ACCEPTOR SPECIFICITIES, DOMAINS THAT PROMOTE IN VITRO PROTEIN FOLDING, AND METHODS FOR THEIR USE

(75) Inventors: Pradman Qasba, Bethesda, MD (US); Boopathy Ramakrishnan, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 203 days.

(21) Appl. No.: 11/178,230

(22) Filed: Jul. 8, 2005

(65) Prior Publication Data

US 2006/0084162 A1 Apr. 20, 2006

Related U.S. Application Data

(63) Continuation of application No. PCT/US2004/000470, filed on Jan. 9, 2004.

(60) Provisional application No. 60/439,298, filed on Jan. 10, 2003, provisional application No. 60/450,250, filed on Feb. 25, 2003.

(51) Int. Cl.
*C12N 9/10* (2006.01)
*C12P 19/28* (2006.01)
*C07H 21/04* (2006.01)

(52) U.S. Cl. .......................... 435/15; 435/85; 435/193; 536/23.2

(58) Field of Classification Search .................. None
See application file for complete search history.

(56) References Cited

FOREIGN PATENT DOCUMENTS

WO WO-2005/056783 A1 6/2005

OTHER PUBLICATIONS

Schwientek et al., Cloning of a novel member of the UDP-galactose:beta-N-acetylglucosamine beta1, 4-galactosyltransferase family, beta4gal-T4 involved in glycosphingolipid biosynthesis. J. Biol. Chem., 1998, vol. 273(45): 29331-29340.*
Jenis, D. M., et al., "Increased activity of a beta-galactosyltransferase in tissues of rats bearing prostate and mammary adenocarcinomas", *Cancer Biochem Biophys*, 6 (1), (1982),37-45.
Keusch, J. , et al., "The effect on IgG glycosylation of altering beta1,4-galactosyltransferase-1 activity in B cells", *Glycobiology*, 8(12), (1998), 1215-1220.
Zhang, S. W., et al., "Effect of p58GTA on beta-1,4-galactosyltransferase 1 activity and cell-cycle in human hepatocarcinoma cells", *Mol. Cell Biochemistry*, 221 (1-2), (May 2001), 161-168.
Y. Zhang et al., "Role of a conserved acidic cluster in bovine beta 1,4 galactosyltransferase-1 probed by mutagenesis of a bacterially expressed recombinant enzyme", Glycobiology, vol. 9, No. 8, pp. 815-822 (1999).
B. Ramakrishnan et al., "Mutation of Arg 228 to Lysine Enhances the Glucosyltransferase Activity of beta 1, 4-Galactosyltransferase-1", Glycobiology, vol. 12, No. 10, (2002).
H. Bakker et al., "A *Lymnaea stagnalis* Gene, with Sequence Similarity to that of Mammalian beta 1 → 4-Galactosyltransferases, Encodes a Novel UDP-GlcNAc:GlcNAc beta—R beta 1 → 4-*N*-Acetylglucosaminyltransferase" Journ. of Bio.Chem., vol. 269, No. 48, pp. 30326-30333 (1994).
B. Ramakrishnan et al., "Mutation of Arginine 228 Residue to Lysine Enhances the Glucosyltransferase Activity of Bovine beta-1,4-Galactosyltransferase I", Biochemistry, vol. 44, No. 9, pp. 3201-3210 (2005).

* cited by examiner

*Primary Examiner*—Rebecca E. Prouty
*Assistant Examiner*—Ganapathirama Raghu
(74) *Attorney, Agent, or Firm*—Edwards Angell Palmer & Dodge LLP; Peter F. Corless; Christine C. O'Day

(57) ABSTRACT

Disclosed are methods and compositions that can be used to synthesize oligosaccharides; mutants of galactosyltransferases having altered donor and acceptor specificity; methods for increasing the immunogenicity of an antigen; and polypeptide stem regions that can be used to promote in vitro folding of polypeptides, such as the catalytic domain from a galactosyltransferase.

7 Claims, 9 Drawing Sheets

```
 45
  R  D  L  R  R  L  P  Q  L  V  G  V  H  P  P  L  Q  G  S  S  Q  A  A  A  A  I  G  Q
 CGAGACCTAAGACGCCTGCCTCAGCTGGTCGGAGTCCACCCACCGCTTCAGGGAAGCTCTCAGGCCGCCGCCGCTATCGGGCAG

P  S  G  E  L  R  L  R  G  V  A  P  P  P  P  L  Q  N  S  S  K  P  R  A  R  A  P  S
 CCCTCCGGGGAGCTCCGGCTGCGAGGGGTCGCACCGCCGCCGCCTTTGCAGAACTCTTCCAAGCCGCGGGCGCGGGCCCCCTCC

N  L  D  A  Y  S  H  P  G  P  G  P  G  P  G  S  N  L  T  S  A  P  V  P  S  T  T  T
 AACCTAGACGCGTACTCTCACCCCGGCCCTGGCCCGGGCCCGGGGAGCAACTTGACTTCGGCCCCAGTGCCCTCCACCACAACA
 129
  R  S  L  T  A  C  P  E  E  S  P  L  L  V  G  P  M  L  I  E  F  N  I  P  V  D  L  K
 CGCTCGCTGACCGCATGCCCTGAGGAGTCCCCGCTGCTCGTCGGCCCCATGCTGATTGAGTTTAACATACCTGTGGACCTGAAG

L  V  E  Q  Q  N  P  K  V  K  L  G  G  R  Y  T  P  M  D  C  I  S  P  H  K  V  A  I
 CTTGTGGAGCAGCAGAACCCGAAGGTGAAGTTGGGTGGTCGCTACACCCCCATGGACTGCATCTCTCCTCACAAGGTGGCCATC

I  I  P  F  R  N  R  Q  E  H  L  K  Y  W  L  Y  Y  L  H  P  I  L  Q  R  Q  Q  L  D
 ATCATTCCATTCCGCAACCGGCAGGAACACCTCAAGTACTGGCTGTATTACTTGCACCCAATCCTACAGCGTCAGCAGTTAGAC

Y  G  I  Y  V  I  N  Q  A  G  E  S  M  F  N  R  A  K  L  L  N  V  G  F  K  E  A  L
 TATGGCATCTATGTTATCAACCAGGCTGGAGAGTCCATGTTCAACCGCGCAAAGCTCCTCAATGTTGGCTTTAAAGAGGCCTTG

K  D  Y  D  Y  N  C  F  V  F  S  D  V  D  L  I  P  M  N  D  H  N  T  Y  R  C  F  S
 AAGGACTATGACTACAACTGCTTTGTGTTTAGCGATGTGGACCTCATCCCAATGAACGACCATAACACCTACAGGTGCTTTTCA

Q  P  R  H  I  S  V  A  M  D  K  F  G  F  S  L  P  Y  V  Q  Y  F  G  G  V  S  A  L
 CAGCCACGGCACATTTCTGTAGCAATGGATAAGTTTGGATTTAGCCTACCTTACGTGCAGTATTTTGGAGGTGTCTCTGCTCTA

S  K  Q  Q  F  L  S  I  N  G  F  P  N  N  Y  W  G  W  G  G  E  D  D  D  I  Y  N  R
 AGTAAACAACAGTTTCTCAGCATCAATGGATTTCCTAATAACTACTGGGGCTGGGGAGGTGAAGATGATGACATTTATAACAGA

L  A  F  R  G  M  S  V  S  R  P  N  A  V  I  G  K  T  R  M  I  R  H  S  R  D  K  K
 TTAGCTTTTAGAGGCATGTCTGTGTCTCGCCCAAATGCTGTGATCGGGAAGACCCGGATGATCCGCCACTCGAGAGACAAGAAA

N  E  P  N  P  Q  R  F  D  R  I  A  H  T  K  E  T  M  L  S  D  G  L  N  S  L  T  Y
 AATGAACCTAATCCTCAGAGGTTTGACCGAATTGCACATACAAAGGAGACAATGCTCTCTGATGGTTTGAACTCACTCACCTAC

M  V  L  E  V  Q  R  Y  P  L  Y  T  K  I  T  V  D  I  G  T  P  S
 ATGGTGTTAGAGGTCCAGAGGTACCCGTTGTATACCAAAATCACAGTGGACATCGGGACGCCGAGC
```

*Fig. 3A*

```
 42
  R  D  L  S  R  L  P  Q  L  V  G  V  S  T  P  L  Q  G  G  S  N  S  A  A  A  I  G  Q
CGCGACCTGAGCCGCCTGCCCCAACTGGTCGGAGTCTCCACACCGCTGCAGGGCGGCTCGAACAGTGCCGCCGCCATCGGGCAG

S  S  G  E  L  R  T  G  G  A  R  P  P  P  P  L  G  A  S  S  Q  P  R  P  G  G  D  S
TCCTCCGGGGAGCTCCGGACCGGAGGGGCCCGGCCGCCGCCTCCTCTAGGCGCCTCCTCCCAGCCGCGCCCGGGTGGCGACTCC

S  P  V  V  D  S  G  P  G  P  A  S  N  L  T  S  V  P  V  P  H  T  T  A  L  S  L  P
AGCCCAGTCGTGGATTCTGGCCCTGGCCCCGCTAGCAACTTGACCTCGGTCCCAGTGCCCCACACCACCGCACTGTCGCTGCCC

A  C  P  E  E  S  P  L  L  V  G  P  M  L  I  E  F  N  M  P  V  D  L  E  L  V  A  K
GCCTGCCCTGAGGAGTCCCCGCTGCTTGTGGGCCCCATGCTGATTGAGTTTAACATGCCTGTGGACCTGGAGCTCGTGGCAAAG
 124
  Q  N  P  N  V  K  M  G  G  R  Y  A  P  R  D  C  V  S  P  H  K  V  A  I  I  I  P  F
CAGAACCCAAATGTGAAGATGGGCGGCCGCTATGCCCCCAGGGACTGCGTCTCTCCTCACAAAGTGGCCATCATCATTCCATTC

R  N  R  Q  E  H  L  K  Y  W  L  Y  Y  L  H  P  V  L  Q  R  Q  Q  L  D  Y  G  I  Y
CGCAACCGGCAGGAGCACCTCAAGTACTGGCTATATTATTTGCACCCAGTCCTGCAGCGCCAGCAGCTGGACTATGGCATCTAT

G  I  Y  V  I  N  Q  A  G  D  T  I  F  N  R  A  K  L  L  N  V  G  F  Q  E  A  L  K
GGCATCTATGTTATCAACCAGGCGGGAGACACTATATTCAATCGTGCTAAGCTCCTCAATGTTGGCTTTCAAGAAGCCTTGAAG

D  Y  D  Y  T  C  F  V  F  S  D  V  D  L  I  P  M  N  D  H  N  A  Y  R  C  F  S  Q
GACTATGACTACACCTGCTTTGTGTTTAGTGACGTGGACCTCATCCCAATGAATGACCATAATGCGTACAGGTGTTTTTCACAG

P  R  H  I  S  V  A  M  D  K  F  G  F  S  L  P  Y  V  Q  Y  F  G  G  V  S  A  L  S
CCACGGCACATTTCCGTTGCAATGGATAAGTTTGGATTCAGCCTACCTTATGTTCAGTATTTTGGAGGTGTCTCTGCTCTAAGT

K  Q  Q  F  L  T  I  N  G  F  P  N  N  Y  W  G  W  G  G  E  D  D  D  I  F  N  R  L
AAACAACAGTTTCTAACCATCAATGGATTTCCTAATAATTATTGGGGCTGGGGAGGAGAAGATGATGACATTTTTAACAGATTA

V  F  R  G  M  S  I  S  R  P  N  A  V  V  G  R  C  R  M  I  R  H  S  R  D  K  K  N
GTTTTTAGAGGCATGTCTATATCTCGCCCAAATGCTGTGGTCGGGAGGTGTCGCATGATCCGCCACTCAAGAGACAAAAAAAAT

E  P  N  P  Q  R  F  D  R  I  A  H  T  K  E  T  M  L  S  D  G  L  N  S  L  T  Y  Q
GAACCCAATCCTCAGAGGTTTGACCGAATTGCACACACAAAGGAGACAATGCTCTCTGATGGTTTGAACTCACTCACCTACCAG

V  L  D  V  Q  R  Y  P  L  Y  T  Q  I  T  V  D  I  G  T  P  S
GTGCTGGATGTACAGAGATACCCATTGTATACCCAAATCACAGTGGACATCGGGACACCGAGC
```

CATALYTIC DOMAINS OF β(1,4)-GALACTOSYLTRANSFERASE I HAVING ALTERED DONOR AND ACCEPTOR SPECIFICITIES, DOMAINS THAT PROMOTE IN VITRO PROTEIN FOLDING, AND METHODS FOR THEIR USE

PRIORITY OF INVENTION

This application is a continuation under 35 U.S.C. 111(a) of International Application No. PCT/US2004/000470 filed Jan. 9, 2004, and published in English as WO 2004/063344 on Jul. 29, 2004, which claims priority from U.S. Provisional Application No. 60/439,298, filed 10 Jan. 2003, and U.S. Provisional Application No. 60/450,250, filed 25 Feb. 2003, which are incorporated herein by reference.

GOVERNMENT FUNDING

The invention described herein was developed with support from the National Institutes of Health, under contract NO1-CO-12400. The U.S. Government may have certain rights in the invention.

FIELD OF THE INVENTION

The invention relates generally to β(1,4)-galactosyltransferase I mutants having altered donor and acceptor specificities, and methods of use thereof. In addition, the invention relates to methods for using the β(1,4)-galactosyltransferase I mutants to increase the immunogenicity of an antigen, such as vaccines, and for synthesizing saccharide compositions.

BACKGROUND OF THE INVENTION

Oligosaccharides are chains composed of saccharide units, which are commonly known as sugars. Of the biological polymer families, oligosaccharides are the least studied, due in part to the difficulty of sequencing and synthesizing their complex sugar chain. Currently, no generally applicable synthetic technique for synthesizing oligosaccharides is available.

Intensive research efforts have been devoted to carbohydrates and molecules comprising carbohydrate fragments, such as glycolipids and glycoproteins. Research interest in these moieties has been largely due to the recognition that interaction between proteins and carbohydrates are involved in a wide array of biological recognition events, including fertilization, molecular targeting, intracellular recognition, and viral, bacterial, and fungal pathogenesis. It is now widely appreciated that the oligosaccharide portions of glycoproteins and glycolipids mediate cell-cell interactions, cell-ligand interactions, cell-extracellular matrix interactions, and cell-pathogen interactions.

It is thought that many of these interactions can be inhibited by oligosaccharides that have the same sugar sequence and stereochemistry found on the active portion of a glycoprotein or glycolipid involved in the interactions. The oligosaccharides are believed to compete with the glycoproteins and glycolipids for binding sites on the receptor proteins. For example, the disaccharide galactosyl-β(1,4)-N-acetylglucosamine is believed to be one component of the glycoprotein which interacts with receptors in the plasma membrane of liver cells. Thus, oligosaccharides and other saccharide compositions that mimic ligands recognized and bound by cellular receptors are thought to be useful in applications that include diagnostics and therapeutics.

In addition to mediating numerous cellular interactions, many oligosaccharides are recognized by the immune system. For example, Anti-Gal, a naturally occurring antibody present in all humans, specifically interacts with the carbohydrate epitope Gal-α(1-3)Gal-β(1-4)GlcNAc-R (α-galactosyl epitope). This antibody does not interact with any other known carbohydrate epitope produced by mammalian cells (Galili, *Springer Seminar Immunopathology*, 15:153 (1993)). Anti-Gal constitutes approximately 1% of circulating IgG (Galili et al., *J. Exp. Med.*, 160:1519 (1984)) and is also found in the form of IgA and IgM (Davine et al., *Kidney Int.*, 31:1132 (1987); Sandrin et al., *Proc. Natl. Acad. Sci.*, 90:11391 (1993)). It is produced by 1% of circulating B-lymphocytes (Galili et al., *Blood*, 82:2485 (1993)). Accordingly, the ability of carbohydrates to elicit an immune response can be utilized to increase the effectiveness of vaccines against many types of pathogens by linking such a carbohydrate to a vacccine to increase the immune response to the vaccine.

There has been relatively little effort to test oligosaccharides as therapeutic agents for humans or animal diseases however, as methods to synthesize oligosaccharides have been unavailable as noted above. Limited types of small oligosaccharides can be custom-synthesized by organic chemical methods, but the cost of such compounds is typically prohibitively high. In addition, it is very difficult to synthesize oligosaccharides stereospecifically and the addition of some sugars, such as sialic acid and fucose, has not been effectively accomplished because of the extreme lability of their bonds. Improved, generally applicable methods for oligosaccharide synthesis are thereby desired for the production of large amounts of widely varying oligosaccharides for therapeutic purposes. Accordingly, the present invention provides enzymes and methods that can be used to promote the chemical linkage of numerous sugars that have previously been difficult to link.

SUMMARY OF THE INVENTION

The invention provides altered β(1,4)-galactosyltransferase I catalytic domains that catalyze the formation of a glucose-β(1,4)-N-acetylglucosamine bond at a greater rate than the catalytic domain of the corresponding wild-type enzyme. The invention also provides β(1,4)-galactosyltransferase I catalytic domains that catalyze formation of N-acetylgalactosamine-β(1,4)-N-acetylglucosamine bonds; N-acetylgalactosamine-β(1,4)-glucose bonds; N-acetylglucosamine-β(1,4)-N-acetylglucosamine bonds; mannose-β(1,4)-N-acetylglucosamine bonds; and galactose-β(1,4)-N-acetylglucosamine-6-$SO_3$ bonds. The invention also provides polypeptides that contain each of the aforementioned catalytic domains.

Also provided by the invention are amino acid segments that promote in vitro folding of catalytic domains of galactosyltransferases, such as β(1,4)-galactosyltransferase I, and mutants of galactosyltransferases.

The invention provides nucleic acid segments that encode the aforementioned β(1,4)-galactosyltransferase I catalytic domains. Expression cassettes and cells that include nucleic acid segments that encode the aforementioned β(1,4)-galactosyltransferase I catalytic domains are also provided.

Additionally provided are methods to synthesize a glucose-β(1,4)-N-acetylglucosamine moiety; an N-acetylgalactosamine-β(1,4)-N-acetylglucosamine moiety; an N-acetylgalactosamine-β(1,4)-glucose moiety; an N-acetylglucosamine-β(1,4)-N-acetylglucosamine moiety; a mannose-β(1,4)-N-acetylglucosamine moiety; and a galactose-β(1,4)-N-acetylglucosamine-6-$SO_3$ moiety.

The invention also provides methods to increase the immunogenicity of an antigen, and methods to prepare an oligosaccharide composition, including those having a defined sequence.

Further provided by the invention are oligosaccharides produced through use of the catalytic domains and methods disclosed herein.

BRIEF DESCRIPTION OF THE FIGURES

FIG. 3 illustrates the cDNA sequence of the inserts and the derived protein sequences of the constructs in the pET23a vector used for studying the effect of the N-terminal stem region (SR) on the solubility and folding of the catalytic domain (CD) of β4Gal-T. (A) Sequence of bovine SRCD β4Gal-T1 having Ser 96 in the wild-type of β4Gal-T1 mutated to Ala 96, corresponding to SEQ ID NO: 9. (B) Sequence of human SRCDβ4Gal-T1, corresponding to SEQ ID NO: 6. The numbers above the amino acids correspond to the residues that delineate the stem region. An 11 amino acid extension (not shown) is located at the amino-terminal end of the protein and is coded by the pET23a vector leader sequence. The stem region sequence is shaded, followed by the catalytic domain (CD) sequence. The primers used for PCR amplification are underlined.

DETAILED DESCRIPTION OF THE INVENTION

Figure 1A:
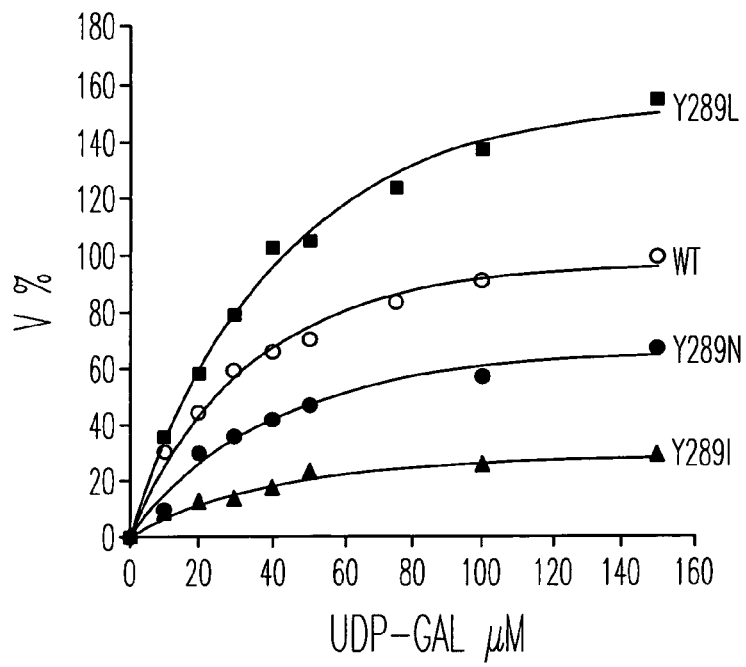
FIG. 1 illustrates the catalytic activity of the wt-Gal-T1 and the mutants Y289L, Y289I, and Y289N. (A) Gal-T activity of wt-Gal-T1 and of mutants at the saturating concentrations of β-benzyl-GlcNAc as the acceptor. (B) GalNAc-T activity of the wt-Gal-T1 and of mutants. The activities are measured with 50 mM β-benzyl-GlcNAc as acceptors at different concentrations of the donor. The Gal-T activity of the wt-Gal-T1 was measured with only 10 mM β-benzyl-GlcNAc because it exhibited inhibition at 50 mM concentration.

β(1,4)-galactosyltransferase I catalyzes the transfer of galactose from the donor, UDP-galactose, to an acceptor, N-acetylglucosamine, to form a galactose-β(1,4)-N-acetylglucosamine bond. This reaction allows galactose to be linked to an N-acetylglucosamine that may itself be linked to a variety of other molecules. Examples of these molecules include other sugars and proteins. The reaction can be used to make many types of molecules having great biological significance. For example, galactose-β(1,4)-N-acetylglucosamine linkages are important for many recognition events that control how cells interact with each other in the body, and how cells interact with pathogens. In addition, numerous other linkages of this type are also very important for cellular recognition and binding events as well as cellular interactions with pathogens, such as viruses. Therefore, methods to synthesize these types of bonds have many applications in research and medicine to develop pharmaceutical agents and improved vaccines that can be used to treat disease.

The present invention is based on the surprising discovery that the enzymatic activity of β(1,4)-galactosyltransferase can be altered such that the enzyme can make chemical bonds that are very difficult to make by other methods. These alterations involve mutating the enzyme such that the mutated enzyme can transfer many different types of donors, sugars for example, to many different types of acceptors. Therefore, the mutated β(1,4)-galactosyltransferases of the invention can be used to synthesize a variety of products that, until now, have been very difficult and expensive to produce.

The invention also provides amino acid segments that promote the proper folding of a galactosyltransferase catalytic domain. The amino acid segments may be used to properly fold the galactosyltransferase catalytic domains of the invention and thereby increase their activity. The amino acid segments may also be used to increase the activity of galactosyltransferases that are produced recombinantly. Accordingly, use of the amino acid segments according to the invention allows for production of β(1,4)-galactosyltransferases having increased enzymatic activity relative to β(1,4)-galactosyltransferases produced in the absence of the amino acid segments.

Definitions:

Abbreviations: stem region/catalytic domain β(1,4)-Galactosyltransferase I (SRCDβ4Gal-T1); catalytic domain of β(1,4)-Galactosyltransferase I (CDβ4Gal-T1); β(1,4)-Galactosyltransferase I (β4Gal-T1); catalytic domain (CD); stem region (SR); wild-type (wt); galactosyltransferase activity (Gal-T); beta-mercaptoethanol (β-ME); N-acetylgalactosamine transferase activity (GalNAc-T); α-Lactalbumin (LA).

The term "acceptor" refers to a molecule or structure onto which a donor is actively linked through action of a catalytic domain of a galactosyltransferase, or mutant thereof. Examples of acceptors include, but are not limited to, carbohydrates, glycoproteins, and glycolipids.

The term "catalytic domain" refers to an amino acid segment which folds into a domain that is able to catalyze the linkage of a donor to an acceptor. For example, a catalytic domain may be from, but is not limited to, bovine β(1,4)-Galactosyltransferase I (Seq ID NO: 5), the catalytic domain from human β(1,4)-Galactosyltransferase I (Seq ID NO: 3), or the catalytic domain from mouse β(1,4)-Galactosyltransferase I (Seq ID NO: 4). A catalytic domain may have an amino acid sequence found in a wild-type enzyme, or may have an amino acid sequence that is different from a wild-type sequence. For example, a catalytic domain may have an amino acid sequence that corresponds to amino acid residues 130-402 of SEQ ID NO: 5, expect that the lysine is exchanged with arginine at amino acid position 228.

The term "donor" refers to a molecule that is actively linked to an acceptor molecule through the action of a catalytic domain of a galactosyltransferase, or mutant thereof. A donor molecule can include a sugar, or a sugar derivative. Examples of donors include, but are not limited to, UDP-galactose, UDP-mannose, UDP-N-acetylglucosamine, UDP-glucose, GDP-mannose, UDP-N-acetylgalactosamine, UDP-glucuronic acid, GDP-Fucose, and CMP-N-acetylneuraminic acid. Donors include sugar derivatives that include active groups, such as cross-linking agents or labeling agents. Accordingly, oligosaccharides may be prepared according to the methods of the invention that include a sugar derivative having a desired characteristic.

"Expression cassette" as used herein means a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The expression cassette may be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The terms oligosaccharide and polysaccharide are used interchangeably herein. These terms refer to saccharide chains having two or more linked sugars. Oligosaccharides and polysaccharides may be homopolymers and heteropolymers having a random sugar sequence or a preselected sugar sequence. Additionally, oligosaccharides and polysaccharides may contain sugars that are normally found in nature, derivatives of sugars, and mixed polymers thereof.

"Polypeptides" and "Proteins" are used interchangeably herein. Polypeptides and proteins can be expressed in vivo through use of prokaryotic or eukaryotic expression systems. Many such expressions systems are known in the art and are commercially available. (Clontech, Palo Alto, Calif.; Stratagene, La Jolla, Calif.). Examples of such systems include, but are not limited to, the T7-expression system in prokaryotes and the bacculovirus expression system in eukaryotes. Polypeptides can also be synthesized in vitro, e.g., by the solid phase peptide synthetic method or by in vitro transcription/translation systems. Such methods are described, for example, in U.S. Pat. Nos. 5,595,887; 5,116,750; 5,168,049 and 5,053,133; Olson et al., *Peptides,* 9, 301, 307 (1988). The solid phase peptide synthetic method is an established and widely used method, which is described in the following references: Stewart et al., *Solid Phase Peptide Synthesis,* W. H. Freeman Co., San Francisco (1969); Merrifield, *J. Am. Chem. Soc.,* 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., *Meth. Enzymol.,* 287, 233 (1997). These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

The polypeptides of the invention include polypeptides having amino acid exchanges, i.e., variant polypeptides, so long as the polypeptide variant is biologically active. The variant polypeptides include the exchange of at least one amino acid residue in the polypeptide for another amino acid residue, including exchanges that utilize the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, N-methyl-alanine, para-benzoyl-phenylalanine, phenylglycine, propargylglycine, sarcosine, N-acetylserine, N-formylmethionine, 3-methylhistidine, 5-hydroxylysine, and other similar amino acids and imino acids and tert-butylglycine.

Conservative amino acid exchanges are preferred and include, for example; aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid exchange also includes groupings based on side chains. Members in each group can be exchanged with another. For example, a group of amino acids having aliphatic side chains is glycine, alanine, valine, leucine, and isoleucine. These may be exchanged with one another. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

I. β(1,4)-Galactosyltransferase I Catalytic Domains of the Invention.

A. Catalytic Domains that Catalyze the Formation of a Bond Between a Donor and an Acceptor to Form glucose-β(1,4)-N-acetylglucosamine Bonds.

It has been discovered that mutation of the donor binding site of β(1,4)-galactosyltransferase I can broaden the donor specificity of the enzyme. More specifically, it has been determined that substitution of amino acid residues located in the donor binding site of β(1,4)-galactosyltransferase I to provide greater flexibility and decreased steric hindrance allow glucose to be bound and chemically bonded to N-acetylglucosamine. Such mutations provide for broadened donor binding, such as binding of glucose, while still preserving interaction with amino acid residues active during catalytic bond formation between the donor and the acceptor. Without being bound by any theory, an example of a catalytic residue thought to be important for catalysis is a glutamic acid positioned at amino acid position 317 (E317) in the bovine β(1,4)-galactosyltransferase I. This glutamic acid in bovine β(1,4)-galactosyltransferase I corresponds to a glutamic acid residue at amino acid position 313 and at amino acid position 314 in the human and mouse β(1,4)-galactosyltransferase I respectively. Accordingly, the invention provides β(1,4)-galactosyltransferase I mutants having amino acid substitutions, insertions, and deletions that provide greater flexibility and decreased steric hindrance in the donor binding site to allow the mutated β(1,4)-galactosyltransferase I to catalyze chemical bonding of the donor to an acceptor, such as N-acetylglucosamine or glucose.

In some embodiments, the catalytic domains of the invention have an arginine exchanged with another amino acid at an amino acid position corresponding to 228 in the bovine β(1,4)-galactosyltransferase I (SEQ ID NO: 5). An example of a specific exchange is R228K. The corresponding arginine in the human and mouse β(1,4)-galactosyltransferase I is located at amino acid position 224 and 225 (SEQ ID Nos: 3 and 4 respectively). In mouse, human, and bovine β(1,4)-galactosyltransferase I, the arginine is located within the amino acid sequence FNRAKLL (SEQ ID NO: 1). Accordingly, those of skill in the art can readily determine an equivalent amino acid in other β(1,4)-galactosyltransferase I catalytic domains.

In other embodiments, the catalytic domains of the invention have an arginine exchanged with another amino acid at an amino acid position corresponding to 228, and an alanine exchanged with another amino acid at an amino acid position corresponding to 229 in the bovine β(1,4)-galactosyltransferase I.

Such catalytic domains are exemplified by a catalytic domain of bovine β(1,4)-galactosyltransferase I having the arginine at amino acid position 228 exchanged with lysine (R228K), and the alanine at amino acid position 229 exchanged with glycine (A229G). The corresponding alanine in the human and mouse β(1,4)-galactosyltransferase I is located at amino acid position 225 and 226 (SEQ ID Nos: 3 and 4 respectively). In mouse, human, and bovine β(1,4)-galactosyltransferase I, the arginine is located within the amino acid sequence FNRAKLL (SEQ ID NO: 1). Accordingly, those of skill in the art can readily determine an equivalent amino acid in other β(1,4)-galactosyltransferase I catalytic domains.

B. Catalytic Domains that Catalyze the Formation of a Bond Between a Donor and an Acceptor to Form N-acetylgalactosamine-β(1,4)-N-acetylglucosamine Bonds.

It was postulated that formation of a hydrogen bond between N-acetylgalactosamine and an amino acid residue adjoining the donor binding site in β(1,4)-galactosyltransferase I is responsible for poor transfer of N-acetylgalactosamine to an acceptor. It was also postulated that mutation of one or more amino acid residues in the donor binding site in β(1,4)-galactosyltransferase I to eliminate hydrogen bond formation with N-acetylgalactosamine allows the mutated β(1,4)-galactosyltransferase I to transfer N-acetylgalactosamine from a donor to an acceptor more efficiently. Therefore, the invention includes mutants of β(1,4)-galactosyltransferase I in which hydrogen bonds that reduce transfer of N-acetylgalactosamine to an acceptor, such as N-acetylglucosamine or glucose, are reduced or absent.

In some embodiments, the catalytic domains of the invention have a tyrosine exchanged with another amino acid at an amino acid position corresponding to 289 in the bovine β(1,4)-galactosyltransferase I (SEQ ID NO: 5). Examples of specific exchanges are Y289L, Y289I, and Y289N. The corresponding tyrosine in the human and mouse β(1,4)-galactosyltransferase I is located at amino acid position 285 and 286 (SEQ ID Nos: 3 and 4 respectively). In mouse, human, and bovine β(1,4)-galactosyltransferase I, the tyrosine is located within the amino acid sequence YVQYFGG (SEQ ID NO: 2). Accordingly, those of skill in the art can readily determine equivalent amino acids in other #(1,4)-galactosyltransferase I catalytic domains.

Mutants in which the tyrosine corresponding to that located at amino acid position 289 in the bovine β(1,4)-galactosyltransferase I has been exchanged by another amino acid may optionally include a second mutation corresponding to amino acid position 342. Such a mutation may include exchange of cysteine at amino acid position 342 with threonine (C342T). However, other amino acids may be exchanged for cysteine that provide and active catalytic domain.

C. Catalytic Domains that Catalyze the Formation of a Bond Between a Donor and an Acceptor to Form N-acetylgalactosamine-β(1,4)-glucose Bonds.

β(1,4)-galactosyltransferase I mutants, as described herein, that are able to catalyze chemical bond formation of N-acetylgalactosamine to an acceptor may be used in conjunction with α-lactalbumin to catalyze the formation of N-acetylgalactosamine-β(1,4)-glucose bonds.

α-Lactalbumin is a mammary gland-specific calcium-binding protein that alters the sugar acceptor specificity of β(1,4)-galactosyltransferase I toward glucose. Consequently, α-lactalbumin may be used to alter the acceptor specificity β(1,4)-galactosyltransferase I, and mutants thereof that are described herein, to efficiently catalyze N-acetylgalactosamine-β(1,4)-glucose bond formation. Conditions for use of α-lactalbumin in conjunction with a galactosyltransferase, or active domain thereof, have been described (Ramakrishnan et al., *J. Biol. Chem.*, 276:37665 (2001)).

D. Catalytic Domains that Catalyze the Formation of a Bond Between a Donor and an Acceptor to Form N-acetylglucosamine-β(1,4)-N-acetylglucosamine Bonds, oligo N-acetylgalactosamine-β(1,4)-N-acetylglucosamine, and mannose-β(1,4)-N-acetylglucosamine.

The mutations described herein may be combined to create catalytic domains having selectively altered donor specificities. For example, a catalytic domain obtained from bovine β(1,4)-galactosyltransferase I having exchanges at amino acid positions 228 (R228K) and 289 (Y289L) was able to catalyze the linkage of N-acetylglucosamine to N-acetylglucosamine to form a N-acetylglucosamine-β(1,4)-N-acetylglucosamine bond. The same mutant catalytic domain was able to catalyze the linkage of N-acetylgalactosamine to N-acetylglucosamine to form oligo N-acetylgalactosamine-β(1,4)-N-acetylglucosamine. The broadened donor specificity was further demonstrated by the ability of the mutant catalytic domain to catalyze the linkage of mannose to N-acetylglucosamine to form mannose-β(1,4)-N-acetylglucosamine. Accordingly, numerous mutant catalytic domains having altered donor specificity may be created by mutating amino acids corresponding to those at positions corresponding to 228 and 289 of the bovine β(1,4)-galactosyltransferase I. As described above, these amino acid positions may be readily determined in galactosyltransferase enzymes obtained from other organisms, such as humans, and mutated in produce additional catalytic domains having altered donor specificity.

E. Catalytic Domains that Catalyze the Formation of a Bond Between a Donor and an Acceptor Having a Bulky Side-Group to Form for Example, galactose-β(1,4)-N-acetylglucosamine-6-$SO_3$ Bonds.

The acceptor specificity of a catalytic domain obtained from a galactosyltransferase may be altered to create catalytic domains capable of transferring a donor onto an acceptor having a bulky and/or charged side-group.

An example of such an altered catalytic domain obtained from bovine β(1,4)-galactosyltransferase I has substitutions at amino acid positions 279 (K279S) and 280 (F280T). This altered catalytic domain is able to catalyze the transfer of galactose to N-acetylglucosamine-6-$SO_3$ to form galactose-β(1,4)-N-acetylglucosamine-6-$SO_3$. Additional catalytic domains may be created by altering one or more amino acid residues at positions corresponding to 279 and 280 of the bovine β(1,4)-galactosyltransferase I. As described above, these amino acid positions may be readily determined in galactosyltransferase enzymes obtained from other organisms, such as humans, and mutated in produce additional catalytic domains having altered acceptor specificity.

The amino acids at positions corresponding to 279 and 280 in the bovine β(1,4)-galactosyltransferase I may be exchanged individually or together to create many different catalytic domains having altered acceptor sites able to accept numerous acceptors having bulky (sterically large) or charged side-groups. Such altered catalytic domains may be used to catalyze linkage of sugars from a donor to an acceptor having a desired side-chain.

II. Catalytic Domains of the Invention May be Included within Full-Length β(1,4)-galactosyltransferase I Enzymes or in Recombinant Molecules Containing the Catalytic Domains.

Peptides of the invention include isolated catalytic domains, full-length β(1,4)-galactosyltransferase I enzymes containing a catalytic domain of the invention, as well as recombinant polypeptides comprising a catalytic domain of the invention that are linked to additional amino acids. Such polypeptides may be expressed from DNA constructs and expression cassettes that are produced through use of recombinant methods. Such methods have been described. Sambrook et al., Molecular Cloning: A Laboratory Manual, 3rd edition, Cold Spring Harbor Press, Cold Spring Harbor, N.Y. (2001).

Galactosyltransferase enzymes containing a catalytic domain of the invention may be produced in soluble form. Methods that may be used to produce such soluble enzymes have been described (U.S. Pat. No. 5,032,519). Briefly, a hydrophobic transmembrane anchor region of a galactosyltransferase is removed to produce an enzyme that is in soluble form.

Alternatively, β(1,4)-galactosyltransferase enzymes containing a catalytic domain of the invention may be produced such that they are anchored in the membrane of a cell that expresses the galactosyltransferase. Such enzymes may be produced that are anchored in the membranes of prokaryotic and eukaryotic cells. Methods to produce such enzymes have been described (U.S. Pat. No. 6,284,493).

Briefly, in the case of procaryotes, the signal and transmembrane sequences of the galactosyltransferase are replaced by a bacterial signal sequence, capable of effecting localization of the fusion protein to the outer membrane. Suitable signal sequences include, but are not limited to those from the major *E. coli* lipoprotein Lpp and lam B. In addition, membrane spanning regions from Omp A, Omp C, Omp F or Pho E can be used in a tripartite fusion protein to direct proper insertion of the fusion protein into the outer membrane. Any procaryotic cells can be used in accordance with the present invention including but not limited to *E. coli*, *Bacillus* sp., and *Pseudomonas* sp. as representative examples.

In another embodiment, the native transmembrane domain of the galactosyltransferase is replaced by the transmembrane domain of a bacterial outer membrane protein. In this embodiment, the galactosyltransferase signal sequence and the bacterial transmembrane region act in concert to anchor the galactosyltransferase to the bacterial outer cell membrane. Nearly any outer membrane bound protein is suitable for this use including but not limited to Omp A, Omp C, and Omp F, Lpp, and Lam B. The catalytic portion of the galactosyltransferase should be fused to an extracellular loop in the bacterial transmembrane region in order to insure proper orientation of the fusion protein on the outer membrane surface and not in the cytoplasm or periplasm of the cell. Insertion of a protein into such a loop region has been previously reported (Charbit et al., *J. Bacteriology*, 173:262 (1991); Francisco et al., *Proc. Natl. Acad. Sci.*, 89:2713(1992)).

The present invention is also applicable for use with eukaryotic cells resulting in cell surface expression of galactosyltransferases in known culturable eukaryotic cells including but not limited to yeast cells, insect cells, chinese hamster ovary cells (CHO cells), mouse L cells, mouse A9 cells, baby hamster kidney cells, C127 cells, COS cells, Sf9 cells, and PC8 cells.

In another embodiment of the present invention, the transmembrane domain of the galactosyltransferase is replaced by the transmembrane domain of a plasma membrane protein.

The transmembrane domain of any resident plasma membrane protein will be appropriate for this purpose. The transmembrane portions of the M6 P/IGF-II receptor, LDL receptor or the transferrin receptor are representative examples.

In another embodiment the Golgi retention signal of the galactosyltransferase is disrupted by site-directed mutagenesis. This approach mutates the amino acids responsible for localizing the galactosyltransferase to the Golgi compartment. The resultant galactosyltransferase is transported to the plasma membrane where it becomes anchored via its modified transmembrane sequences. Substitution of isoleucine residues for the native amino acids in the transmembrane region of the β(1,4)galactosyltransferase has been shown to preferentially localize the enzyme to the plasma membrane instead of the Golgi apparatus (Masibay et al., *J. Biol. Chem.*, 268:9908 (1993)).

III. A Stem Region that Promotes the In Vitro Folding of a Catalytic Domain of a Galactosyltransferase.

β(1,4)-galactosyltransferase I is a type II Golgi resident protein with a short cytoplasmic tail, a transmembrane domain followed by a stem region and has a globular catalytic domain that faces the Golgi lumen. When the catalytic domain of β(1,4)-galactosyltransferase I is expressed in *E. Coli*, it forms insoluble inclusion bodies. These inclusion bodies can be collected and then solubilized and folded in vitro to produce catalytically active domains. Thus, the in vitro folding efficiency is directly related to the quantity of active enzyme that is produced from the isolated inclusion bodies. Accordingly, methods to increase the in vitro folding efficiency would provide increased production of catalytic domains that can be used to create useful products.

The invention provides materials and methods that improve in vitro folding of catalytic domains from galactosyltransferases that are related to the use of a stem region (for example, SEQ ID NOs: 6 and 7) of β(1,4)-galactosyltransferase I. It has been determined that fusion of a stem region from a β(1,4)-galactosyltransferase I to the amino-terminus of the catalytic domain of a β(1,4)-galactosyltransferase I produces increased in vitro folding efficiency of the catalytic domain. This increase in folding is thought to be universal among β(1,4)-galactosyltransferase I enzymes and was demonstrated with both the bovine and human enzymes.

Figure 8A:
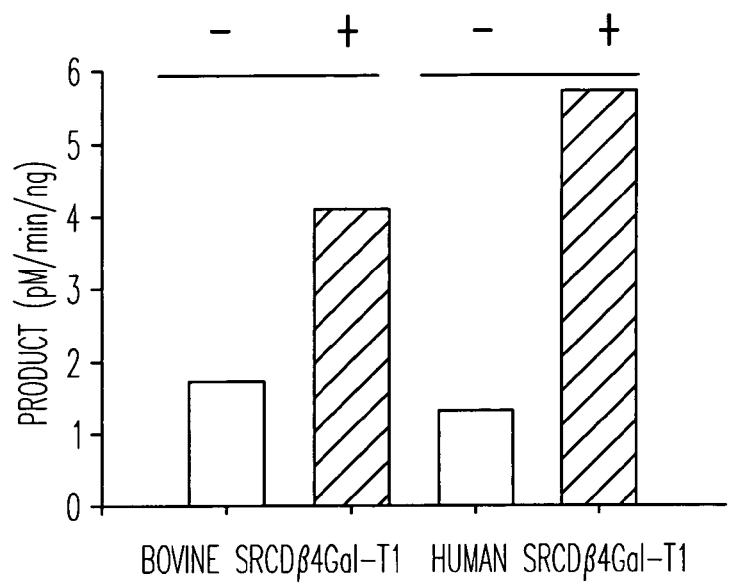
FIG. 8 shows the enzymatic activity of the soluble human and bovine SRCDβ4Gal-T1 proteins before and after UDP-agarose purification. The galactosyltransferase activities were measured as described herein. Specific activities of these proteins before binding ((−), black bars) and of the eluates after passing through the UDP-agarose column ((+), cross-hatched bars) are shown. (A) Buffer condition I (without PEG-4000 and L-arginine), showed more misfolded molecules in the human SRCD β4Gal-T1 compared to bovine SRCDβ4Gal-T1. (B) Condition VIII (with PEG-4000 and L-arginine) showed more properly folded proteins in the human SRCDβ4Gal-T1 compared to bovine SRCDβ4Gal-T1 (black bars). CDβ4Gal-T1 showed difference in the amounts of folded proteins before and after binding on the UDP-agarose columns either with folding condition I or condition VIII (data not shown).
Figure 8B:
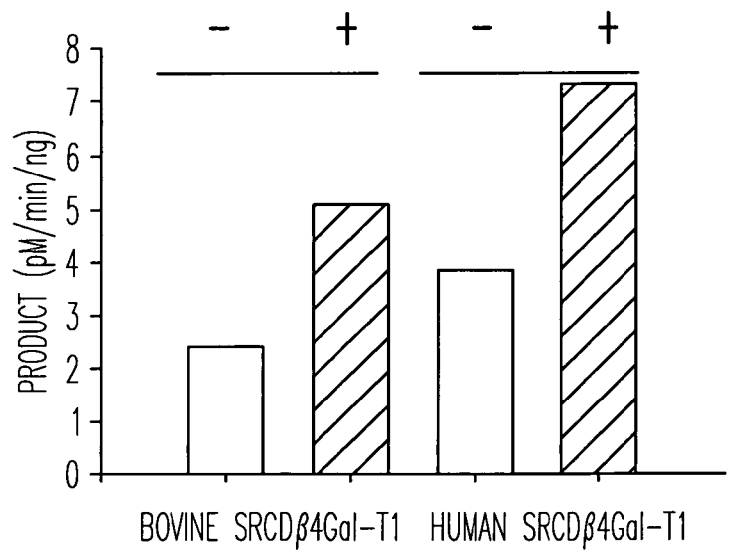
Figure 9:
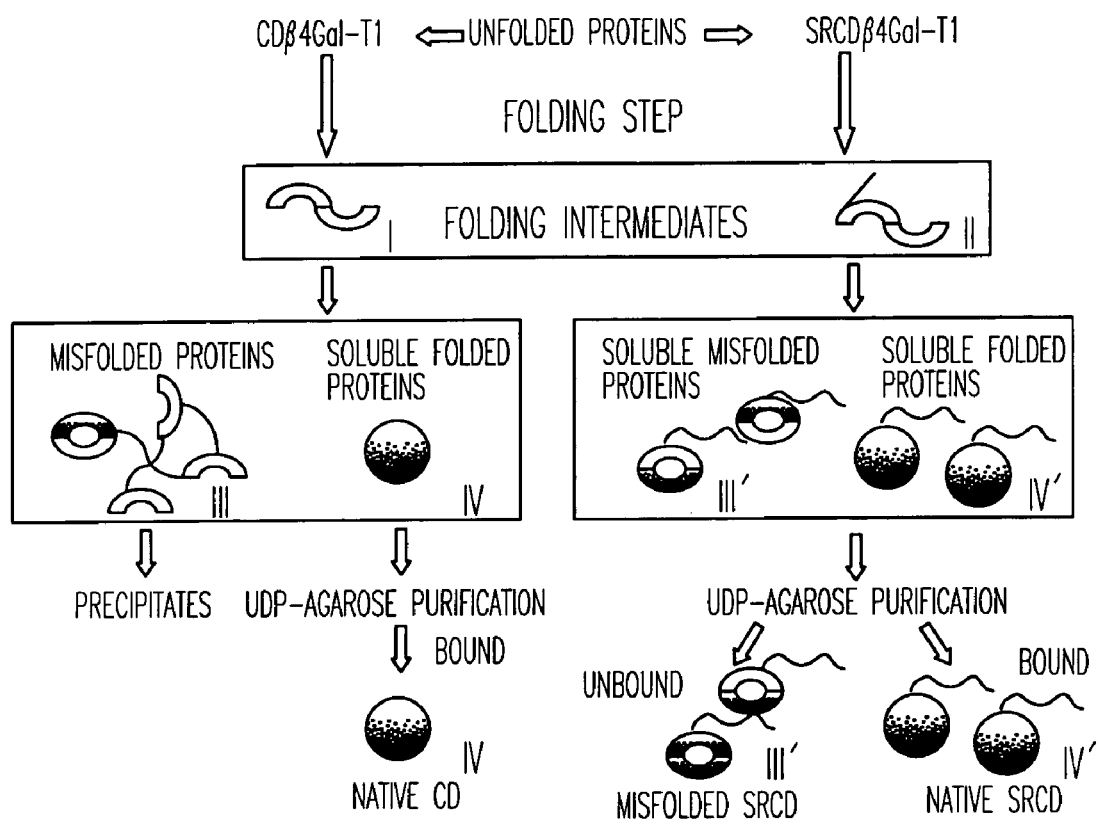
FIG. 9 is a schematic diagram of the in vitro folding of CD and SRCD domains of β4Gal-T1. The unfolded CD and SRCD domains during the in vitro folding step are thought to generate folding intermediates (I) and (II), respectively, which produce misfolded and properly folded molecules. The misfolded molecules of CD, (III) are mostly insoluble and precipitate out, whereas properly folded molecules (IV) are soluble, remain in solution and bind to a UDP-agarose column. SRCD misfolded (III') and properly folded molecules (IV') are mostly soluble. Due to the solubility effect of SR domain the proportion of the properly folded SRCD molecules increased during the folding process. The misfolded SRCD molecules, although soluble, did not significantly bind to UDP-agarose columns (III'). Properly folded SRCD molecules bind (IV') and elute from the UDP-agarose column. The presence of PEG-4000 and L-arginine in the folding solution increased the proportion of the properly folded molecules.

It has been further discovered that inclusion of PEG-4000 and L-Arg in the folding reaction results in a four-fold to seven-fold increase in catalytic domains that are natively folded when compared to refolding of the catalytic domain alone in the absence of PEG-4000 and L-Arg. PEG-4000 and L-arginine are thought to beneficially affect the solubility of folding intermediates of both catalytic domain-proteins (CD-proteins) and stem region/catalytic domain proteins (SRCD-proteins) during in vitro folding or protein obtained from inclusion bodies. The presence of PEG-4000 and L-arginine during in vitro folding enhanced the formation of both native and misfolded molecules. The processes involved are schematically shown in FIG. 9. In the case of CD-proteins, the majority of misfolded proteins are insoluble in the absence of PEG-4000 and L-arginine and thus, they precipitate out during dialysis. This process left behind the properly folded molecules in solution that bound to UDP-agarose and were enzymatically active. (FIG. 8) (Table IX). It is thought that the SR-domain, like PEG-4000 and L-arginine, helped to solubilize the folding intermediates, and hence enhanced the formation of both native and misfolded-SRCD molecules. The presence of PEG-4000 and L-arginine enhanced the solubilization of the folding intermediates of SRCD-molecules even further. The misfolded SRCD proteins, in contrast to the majority of CD-proteins, remained soluble even in the absence of PEG-4000 and L-arginine. Therefore, the misfolded SRCD-proteins were not removed as precipitates during dialysis. Misfolded SRCD-proteins can be separated from properly folded proteins through binding on UDP-agarose columns (Table IX). Thus the SR-domain is thought to act as a solubilizing agent both for the misfolded and folded catalytic domain. It is thought that the increased solubility of SRCD-proteins is produced by preventing aggregation of misfolded proteins. In this respect its mode of action is thought to resemble the action of chaperone proteins. The positive effect of the N-terminal stem region in the folding and stability of the native protein is very useful for producing large quantities of other galactosyltransferase family members.

The in vitro folding efficiency of bovine β(1,4)-galactosyltransferase I was further increased by substituting the cysteine at amino acid position 342 with a threonine (C342T). Analogous mutations can be made in β(1,4)-galactosyltransferase I enzymes from other organisms.

It was determined that the wild-type bovine SRCDβ4Gal-T1, folded and purified from inclusion bodies, was cleaved at Ser96 within the stem region over a short period of time. Therefore, to decrease degradation of bovine SRCDβ4Gal-T1, the serine at amino acid position 96 was exchanged with an Ala to produce S96A-SRCDβ4Gal-T1. After folding and purification from bacterial inclusion bodies, S96A-SRCDβ4Gal-T1 was found to be more stable over a long period of time when compared to SRCDβ4Gal-T1, which did not include the S96A mutation. S96A-SRCDβ4Gal-T1 was used within some of the in vitro folding studies disclosed herein.

The in vitro folding efficiency of catalytic domains that include a stem region in the presence of PEG-4000 and L-Arg was about 50 percent and the solubility of the refolded product was about 90 percent.

Accordingly, the invention includes stem regions from members of the galactosyltransferase family that can be fused to a catalytic domain of a galactosyltransferase to provide increased in vitro folding of the catalytic domain. Such stem regions can be readily determined based on amino acid sequence homology to the bovine stem region and tested for the ability to promote folding of a galactosyltransferase catalytic domain. The invention also includes the mutants disclosed herein and their corresponding analogs in other species.

General methods for isolating and folding inclusion bodies containing galactosyltransferase catalytic domains have been previously described (Ramakrishnan et al., *J. Biol. Chem.*, 276:37665 (2001)). These methods may be used in conjunction with the stem region of the invention, PEG-4000, and L-Arg to increase the folding efficiency of a galactosyltransferase catalytic domain. These methods are described in the examples section herein.

IV. Nucleic Acid Segments Encoding Catalytic Domains of β(1,4)-galactosyltransferase I, Expression Cassettes that Include the Nucleic Acid Segments, and Cells that Include the Nucleic Acid Segments and Expression Cassettes.

The present invention provides isolated nucleic acid segments that encode catalytic domains of β(1,4)-galactosyltransferase I having altered donor or acceptor specificity. The present invention also provides nucleic acid segments that encode amino acid segments that promote proper folding of catalytic domains from galactosyltransferases, such as β(1,4)-galactosyltransferase I.

Nucleic acid sequences encoding human β(1,4)-galactosyltransferase I (SEQ ID NO: 8), as well as other β(1,4)-galactosyltransferases I from other organisms are available. These nucleic acid sequences can be modified to encode the catalytic domains and amino acid segments of the invention through use of well-known techniques (Sambrook et al., Molecular Cloning: A Laboratory Manual, 3rd edition, Cold Spring Harbor Press, Cold Spring Harbor, N.Y. (2001)). For example, a portion of the nucleic acid sequence encoding human β(1,4)-galactosyltransferase I (SEQ ID NO: 8) can be inserted into an expression vector such that an amino acid segment corresponding to the catalytic domain of human β(1,4)-galactosyltransferase I (SEQ ID NO: 6) is expressed upon transformation of a cell with the expression vector. In another example, bovine β(1,4)-galactosyltransferase I can be altered to replace the tyrosine at amino acid position 289 with leucine, isoleucine, or asparagine through use of site-directed mutagenesis (Ramakrishnan et al., *J. Biol. Chem.*, 277:20833 (2002)). Similar methods may be used to produce nucleic acid segments encoding additional mutants and catalytic domains described herein.

The nucleic acid segments of the invention may be optimized for expression in select cells. Codon optimization tables are available. Harlow and Lane, *Antibodies: A Laboratory Manual*, Cold Spring Harbor Laboratory Press, 1988.

The nucleic acid segments can be inserted into numerous types of vectors. A vector may include, but is not limited to, any plasmid, phagemid, F-factor, virus, cosmid, or phage in double or single stranded linear or circular form which may or may not be self transmissible or mobilizable. The vector can also transform a prokaryotic or eukaryotic host either by integration into the cellular genome or exist extrachromosomally (e.g. autonomous replicating plasmid with an origin of replication).

Preferably the nucleic acid segment in the vector is under the control of, and operably linked to, an appropriate promoter or other regulatory elements for transcription in vitro or in a host cell such as a eukaryotic cell or microbe, e.g. bacteria. The vector may be a bi-functional expression vector which functions in multiple hosts. In the case of genomic DNA, this may contain its own promoter or other regulatory elements and in the case of cDNA this may be under the control of a promoter or other regulatory sequences for expression in a host cell.

Specifically included are shuttle vectors by which is meant a DNA vehicle capable, naturally or by design, of replication in two different host organisms, which may be selected from bacteria and eukaryotic cells (e.g. mammalian, yeast or fungal).

The vector may also be a cloning vector which typically contains one or a small number of restriction endonuclease recognition sites at which nucleic acid segments can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance, hygromycin resistance or ampicillin resistance. Many cloning vectors are commercially available (Stratagene, New England Biolabs, Clonetech).

The nucleic acid segments of the invention may also be inserted into an expression vector. Typically an expression vector contains (1) prokaryotic DNA elements coding for a bacterial replication origin and an antibiotic resistance gene to provide for the amplification and selection of the expression vector in a bacterial host; (2) regulatory elements that control initiation of transcription such as a promoter; and (3) DNA elements that control the processing of transcripts such as introns, transcription termination/polyadenylation sequence.

Methods to introduce a nucleic acid segment into a vector are well known in the art (Sambrook et al., 1989). Briefly, a vector into which the nucleic acid segment is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid segment into the vector. The nucleic acid segment that is to be inserted into the vector is treated with one or more restriction enzymes to create a linearized segment having a blunt end, a "sticky" end with a 5' or a 3' overhang, or any combination of the above. The nucleic acid segment may also be treated with a restriction enzyme and subsequently treated with another DNA modifying enzyme. Such DNA modifying enzymes include, but are not limited to, polymerase, exonuclease, phosphatase or a kinase, to create a polynucleic acid segment that has characteristics useful for ligation of a nucleic acid segment into the vector.

The treated vector and nucleic acid segment are then ligated together to form a construct containing a nucleic acid segment according to methods known in the art (Sambrook, 2002). Briefly, the treated nucleic acid fragment and the treated vector are combined in the presence of a suitable buffer and ligase. The mixture is then incubated under appropriate conditions to allow the ligase to ligate the nucleic acid fragment into the vector. It is preferred that the nucleic acid fragment and the vector each have complimentary "sticky" ends to increase ligation efficiency, as opposed to blunt-end ligation. It is more preferred that the vector and nucleic acid fragment are each treated with two different restriction enzymes to produce two different complimentary "sticky" ends. This allows for directional ligation of the nucleic acid fragment into the vector, increases ligation efficiency and avoids ligation of the ends of the vector to reform the vector without the inserted nucleic acid fragment.

Suitable procaryotic vectors include but are not limited to pBR322, pMB9, pUC, lambda bacteriophage, m13 bacteriophage, and Bluescript®. Suitable eukaryotic vectors include but are not limited to PMSG, pAV009/A+, PMTO10/A+, pMAM neo-5, bacculovirus, pDSVE, YIP5, YRP17, YEP. It will be clear to one of ordinary skill in the art which vector or promoter system should be used depending on which cell type is used for a host cell.

The invention also provides expression cassettes which contain a control sequence capable of directing expression of a particular nucleic acid segment of the invention either in vitro or in a host cell. The expression cassette is an isolatable unit such that the expression cassette may be in linear form and functional in in vitro transcription and translation assays. The materials and procedures to conduct these assays are commercially available from Promega Corp. (Madison, Wis.). For example, an in vitro transcript may be produced by placing a nucleic acid segment under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid segment.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. Expression of the nucleic acid segment in the expression cassette may be under the control of a constitutive promoter or an inducible promoter which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source. Numerous termination regions are known in the art. Guerineau et al., *Mol. Gen. Genet.*, 262:141 (1991); Proudfoot, *Cell*, 64:671 (1991); Sanfacon et al., *Genes Dev.*, 5:141 (1991); Munroe et al., *Gene*, 91:151 (1990); Ballas et al., *Nucleic Acids Res.*, 17:7891 (1989); Joshi et al., *Nucleic Acid Res.*, 15:9627 (1987).

The regulatory sequence can be a nucleic acid sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to, enhancers, promoters, repressor binding sites, translation leader sequences, introns, and polyadenylation signal sequences. They may include natural and synthetic sequences as well as sequences which may be a combination of synthetic and natural sequences. While regulatory sequences are not limited to promoters, some useful regulatory sequences include constitutive promoters, inducible promoters, regulated promoters, tissue-specific promoters, viral promoters and synthetic promoters.

A promoter is a nucleotide sequence that controls expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be inducible. Several inducible promoters have been reported (*Current Opinion in Biotechnology*, 7:168 (1996)). Examples include the tetracycline repressor system, Lac repressor system, copper-inducible systems, salicylate-inducible systems (such as the PR1a system). Also included are the benzene sulphonamide—(U.S. Pat. No. 5,364,780) and alcohol—(WO 97/06269 and WO 97/06268) inducible systems and glutathione S-transferase promoters. In the case of a multicellular organism, the promoter can also be specific to a particular tissue or organ or stage of development.

An enhancer is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects.

The expression cassette can contain a 5' non-coding sequence which is a nucleotide sequence located 5' (upstream) to the coding sequence. It is present in the fully processed mRNA upstream of the initiation codon and may affect processing of the primary transcript to mRNA, stability of the mRNA, or translation efficiency (Turner et al., *Molecular Biotechnology*, 3:225 (1995)).

The expression cassette may also contain a 3' non-coding sequence which is a nucleotide sequence located 3' (downstream) to a coding sequence and includes polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The invention also provides a construct containing a vector and an expression cassette. The vector may be selected from, but not limited to, any vector previously described. Into this vector may be inserted an expression cassette through methods known in the art and previously described (Sambrook et al., 1989). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially and methods for their use are known in the art (Clonetech, Promega, Stratagene).

The expression cassette, or a vector construct containing the expression cassette may be inserted into a cell. The expression cassette or vector construct may be carried eposomally or integrated into the genome of the cell.

A variety of techniques are available and known to those skilled in the art for introduction of constructs into a cellular host. Transformation of bacteria and many eukaryotic cells may be accomplished through use of polyethylene glycol, calcium chloride, viral infection, phage infection, electroporation and other methods known in the art. Other transformation methods are available to those skilled in the art, such as direct uptake of foreign DNA constructs (see EP 295959), techniques of electroporation (Fromm et al. *Nature (London)*, 319:791 (1986) or high velocity ballistic bombardment with metal particles coated with the nucleic acid constructs (Kline et al. *Nature (London)* 327:70 (1987), and U.S. Pat. No. 4,945,050).

The selection of an appropriate expression vector will depend upon the method of introducing the expression vector into host cells. Typically an expression vector contains (1) prokaryotic DNA elements coding for a bacterial origin of replication and an antibiotic resistance gene to provide for the amplification and selection of the expression vector in a bacterial host; (2) DNA elements that control initiation of transcription, such as a promoter; (3) DNA elements that control the processing of transcripts, such as introns, transcription termination/polyadenylation sequence; and (4) a reporter gene that is operatively linked to the DNA elements to control transcription initiation. Useful reporter genes include β-galactosidase, chloramphenicol acetyl transferase, luciferase, green fluorescent protein (GFP) and the like.

V. Methods to Synthesize glucose-β(1,4)-N-acetylglucosamine moieties; N-acetylgalactosamine-β(1,4)-N-acetylglucosamine moieties; N-acetylgalactosamine-β(1,4)-glucose moieties: N-acetylglucosamine-β(1,4)-N-acetylglucosamine moieties: mannose-β(1,4)-N-acetylglucosamine moieties: and galactose-β(1,4)-N-acetylglucosamine-6-$SO_3$ moieties.

Catalytic domains of the invention having altered donor and acceptor specificity can be used to catalyze the linkage of numerous sugars from a donor to numerous acceptor sugars. Linkage of sugar derivatives can also achieved through use of the altered catalytic domains of the invention due to their expanded donor and acceptor specificity.

For example, the catalytic domains of section IA can be used to catalyze the linkage of glucose and N-acetylglucosamine; the catalytic domains of section IB can be used to catalyze the linkage of N-acetylgalactosamine and N-acetylglucosamine; many of the catalytic domains described herein can be used in association with α-lactalbumin to catalyze linkage of a sugar to glucose, as described in section IC; the catalytic domains of section ID can be used to catalyze the linkage of N-acetylglucosamine and N-acetylglucosamine, N-acetylgalactosamine to N-acetylglucosamine, and mannose to N-acetylglucosamine; and the catalytic domains of section IE can be used to catalyze the linkage of a donor and an acceptor having a bulky side-group, such as linking galactose to N-acetylglucosamine-6-$SO_3$.

Acceptors may be free in solution or linked to another molecule. For example, an acceptor may be linked to a protein, another sugar, a sugar derivative, and the like. An acceptor may also be linked to a solid support that provides a platform to which donors may be added sequentially to form oligosaccharides, and derivatives thereof, having a specified sequence.

Generally, the linkage between a donor and an acceptor is accomplished by incubating a catalytic domain of the invention with a desired donor and a desired acceptor under conditions of appropriate temperature, pH, and divalent metal concentration to allow linkage of the donor to the acceptor.

For example, the galactose and N-acetylgalactosyltransferase activity of β(1,4)-galactosyltransferase I can be determined using the following assay conditions. A 100 μl incubation mixture containing 50 mM β-benzyl-GlcNAc, 10 mM $MnCl_2$, 10 mM Tris-HCl (pH 8.0), 500 μM UDP-Gal or UDP-GalNAc, and 20 ng of β(1,4)-galactosyltransferase I can be incubated at 37° C. for 10 minutes to promote coupling of a donor sugar to an acceptor sugar. While these conditions are provided as an example, it is understood that many other conditions may be used to chemically link a donor to an acceptor using the altered catalytic domains of the invention.

VI. Methods to Prepare Oligosaccharides.

The invention provides methods to synthesize oligosaccharides, especially oligosaccharides having preselected sequences though use of the altered catalytic domains of the invention. Generally, the methods involve the sequential addition of a sugar, or derivative thereof, to the end of a growing oligosaccharide chain. Such methods have been described using enzymes other than those of the invention (U.S. Pat. No. 6,284,493).

Briefly, a donor and an acceptor may be incubated with an altered catalytic domain of the invention under conditions that allow the donor to be linked to the acceptor. These conditions are described in the examples section herein.

In one example, the donor and the acceptor may be combined with a catalytic domain of the invention in solution. The solution is then incubated to allow the donor to be linked to the acceptor. The newly linked molecule may be isolated and then added to a second solution containing a second donor and a second transferase enzyme. This cycle may be repeated with a specific donor added at each cycle such that an oligosaccharide having a specific sequence is produced.

In another example, an acceptor may be linked to a solid support. The solid support may then be immobilized in a structure such as a column or a tray. A donor and a catalytic domain of the invention can then be incubated with the immobilized acceptor under conditions that allow the donor to be linked to the acceptor. The solid support is then washed to remove any unlinked donor and catalytic domain present. A second donor and a second transferase enzyme can then be added and incubated under conditions that allow the donor to be linked to the acceptor. This cycle can be repeated to allow for the rapid and large-scale production of oligosaccharides having defined sequences. In addition, this method may be readily adapted for use in an automated system. This system may be used without the need for protecting groups on the acceptor or the donor due to the use of enzymes that catalyze the linkage of a given donor to a given acceptor. Accordingly, an advantage of this method is that mild reaction conditions may be used that do not damage the growing oligosaccharide chain. Another advantage of the method is the short cycling time required to add monomers onto the growing oligosaccharide chain due to the lack of a need to protect and deprotect the growing oligosaccharide chain.

Other methods for using the catalytic domains of the invention to synthesize sequences of predetermined oligosaccharides and derivatives thereof may also be used. However, these methods will utilize an galactosyltransferase having an altered acceptor site, an altered donor site, or altered donor and acceptor sites.

VII. Methods to Increase the Immunogenicity of an Antigen.

The invention provides methods to increase the immunogenicity of an antigen. Generally, the methods involve incubating an antigen with a catalytic domain of the invention such that a sugar is transferred from a donor to an acceptor through the action of a catalytic domain.

The methods of the invention may be used in association with nearly any acceptor containing material against which an immune response is desired. For example, sugars may be transferred from a donor to an acceptor that is linked to a whole cell. The cell can then be killed through irradiation or chemical means and administered to an animal to elicit an immune response. Cell membranes may be used in a similar manner. Methods to create an immune response against cells and cell membranes are described in U.S. Pat. No. 6,361,775.

The immunogenicity of a virus or subunit thereof may be increased according to the methods of the invention and used as an improved vaccine. For example, for a virus that contains a glycoprotein as a component of the virion, one or more sugars may be added to the glycoprotein by propagation of the virus in a cell that expresses a catalytic domain of the invention. Alternatively, one or more sugars may be directly added to the glycoprotein using a catalytic domain of the invention. Furthermore, there exist viruses without envelopes that contain complex carbohydrates. Sugars may be added onto these carbohydrates through use of a catalytic domain of the invention.

Viral subunits may be obtained from virions using biochemical methods or they can be expressed by recombinant means in suitable eukaryotic cells. Methods of expressing viral subunits are common in the art. These methods may vary according to the type of virus used. For example, methods of expressing viral subunits are described in the following articles and in the references cited therein: Possee, *Virus Research*, 5:43 (1986); Kuroda et al., *EMBO J.*, 5: 1359 (1986); Doerfler, *Curr. Topics Microbiol. Immunol.*, 131:51 (1986); Rigby, *J. Gen. Virol.*, 64:255 (1983); Mackett et al., In: DNA Cloning, A Practical Approach, Vol II, Ed. D. M. Glover, IRL Press, Washington, D.C. (1985); Rothestein, In: DNA Cloning, A Practical Approach, Supra (1985); Kinney et al., *J. Gen. Virol.*, 69:3005 (1988); Panical et al., *Proc. Natl. Acad. Sci.*, 80:5364 (1983); Small et al., In: Vaccinia Viruses as Vectors for Vaccine Antigens, pp. 175-178, Ed. J. Quinnan, Elsevier, N.Y. (1985).

Viruses for which vaccines are currently available and whose immunogenicity can be improved according to the methods of the invention include influenza virus (Orthomyxovirus); rabies virus (Rhabdovirus); hepatitis B virus (Hepadnavirus); eastern, western and Venezuelan equine encephalitis virus (*Togavirus/Alphavirus* genus); and, Japanese encephalitis virus, tick-borne encephalitis virus and Russian spring-summer encephalitis virus (Flavivirus); Rift Valley fever virus (Bunyavirus)(reviewed: Melnick, In: High Technology Route to Virus Vaccines Ed. Dreesman, Bronson and Kennedy, American Society for Microbiology, Washington, D.C. (1985); Ogra et al., *Prog. Med. Virol.*, 37:156 (1990)). Viruses for which vaccines are not yet commercially available but which may also be useful when treated according to the methods of the invention include, but are not limited to human immunodeficiency and human T-cell leukemia viruses (Retrovirus); respiratory syncytial virus and other paramyxoviruses (Paramyxovirus); herpes simplex viruses types 1 and 2, varicella zoster virus, cytomegalovirus and other herpes viruses (Herpesviruses); dengue virus and Saint Louis encephalitis virus (Flavivirus); hantaan virus (Bunyavirus); Lassa virus (Arenavirus); and, rotavirus (Reovirus). In addition, there exist viral vaccines comprising live attenuated viruses the administration of which to humans is associated with some measure of risk of mild to severe side effects. It is now possible according to the methods of the invention to enhance the immunogenicity of killed virus vaccines which may serve to reduce the use of their live, more risk-associated counterparts. Thus, vaccines which currently comprise live virus, such as measles virus, mumps virus, rubellavirus etc. are all encompassed by the invention.

Vaccines are prepared by suspension of a suitable concentration of an antigen that has been linked to a sugar, through the action of a catalytic domain of the invention, in a pharmaceutically acceptable carrier. The composition of the carrier will depend upon the type of vaccine and the route of administration and will be readily apparent to one skilled in the art. The vaccine may be administered in a dose of $10^2$ to $10^9$ cells per dose (in the case of whole cells) or a similar equivalent of cell membranes. In the case of viral vaccines, virus may be administered in dose ranging from 1 µg to 50 mg of virus per dose, or a similar equivalent of subunit. Determination of the appropriate dosage of vaccine will be apparent to one of skill in the art and will depend upon the antigens comprising the vaccine, the age of the patient and their general and immunological health.

In order to improve the efficacy of vaccines prepared according to the methods of the invention, patients may be pretreated with adjuvant at the site of vaccination several days prior to administration of vaccine. Pretreatment with adjuvant serves to induce migration of macrophages to the site of inoculation, thereby enhancing the rate of phagocytosis of treated antigens. In the case of viral vaccines, patients may be treated with adjuvant and vaccine simultaneously. Adjuvants suitable for this purpose include aluminum hydroxide and like adjuvants.

Vaccines are administered to a mammal, particularly a human, either subcutaneously, intramuscularly, orally, intravenously, intradermally, intranasally or intravaginally. Prior to oral administration, the vaccine can be mixed with a solution containing a sufficient amount of sodium bicarbonate or other suitable compound capable of neutralizing stomach acid (approximately 2 grams). Alternatively, the vaccine usually in lyophilized form, can be formulated as tablets which are treated with a coating capable of resisting stomach acid.

TABLE I

Exemplary Amino Acid Sequences

| SEQ ID NO | Accession Number | Description | Amino Acid Sequence |
|---|---|---|---|
| 3 | BAA06188 | Human β(1,4)galactosyl-transferase (398 AA) | MRLREPLLSRSAAMPGASLQRACRLLVAVCA |
| | | | LHLGVTLVYYLAGRDLSRLPQLVGVSTPLQG |
| | | | GSNSAAAIGQSSGDLRTGGARPPPPLGASSQP |
| | | | RPGGDSSPVVDSGPGPASNLTSVPVPHTTALS |
| | | | LPACPEESPLLVGPMLIEFNMPVDLELVAKQN |
| | | | PNVKMGGRYAPRDGVSPHKVAIIIPFRNRQEH |
| | | | LKYWLYYLHPVLQRQQLDYGIYVINQAGDTI |
| | | | FNRAKLLNVGFQEALKDYDYTCFVFSDVDLI |
| | | | PMNDHNAYRCFSQPRHISVAMDKFGFSLPYV |
| | | | QYFGGVSASSKQQFLTINGFPNNYWGWGGE |
| | | | DDDIFNRLVFRGMSISRPNAVVGTCRMIRHSR |
| | | | DKKNEPNPQRFDRIAHTKETMLSDGLNSLTY |

TABLE I-continued

Exemplary Amino Acid Sequences

| SEQ ID NO | Accession Number | Description | Amino Acid Sequence |
|---|---|---|---|
| | | | QVLDVQRYPLYTQITVDIGTPS |
| 4 | A33396 | Mouse β(1,4) galactosyl-transferase (399 AA) | MRFREQFLGGSAAMPGATLQRACRLLVAVC ALHLGVTLVYYLSGRDLSRLPQLVGVSSTLQ GGTNGAAASKQPPGEQRPRGARPPPPLGVSP KPRPGLDSSPGAASGPGLKSNLSSLPVPTTTG LLSLPACPEESPLLVGPMLIDFNIAVDLELLAK KNPEIKTGGRYSPKDCVSPHKVAIIIPFRNRQE HLKYWLYYLHPILQRQQLDYGIYVINQAGDT MFNRAKLLNIGFQEALKDYDYNCFVFSDVDL IPMDDRNAYRCFSQPRHISVAMDKFGFSLPY VQYFGGVSALSKQQFLAINGFPNNYWGWGG EDDDIFNRLVHKGMSISRPNAVVGRCRMIRH SRDKKNEPNPQRFDRIAHTKETMRFDGLNSL TYKVLDVQRYPLYTQITVDIGTPR |
| 5 | S05018 | Bovine β(1,4)galactosyl-transferase (402 AA) | MKFREPLLGGSAAMPGASLQRACRLLVAVC ALHLGVTLVYYLAGRDLRRLPQLVGVHPPLQ GSSHGAAAIGQPSGELRLRGVAPPPPLQNSSK PRSRAPSNLDAYSHPGPGPGPGSNLTSAPVPS TTTRSLTACPEESPLLVGPMLIEFNIPVDLKLIE QQNPKVKLGGRYTPMDCISPHKVAIIILFRNR QEHLKYWLYYLHPMVQRQQLDYGIYVINQA GESMFNRAKLLNVGFKEALKDYDYNCFVFS DVDLIPMNDHNTYRCFSQPRHISVAMDKFGF SLPYVQYFGGVSALSKQQFLSINGFPNNYWG WGGEDDDIYNRLAFRGMSVSRPNAVIGKCR MIRHSRDKKNEPNPQRFDRIAHTKETMLSDG LNSLTYMVLEVQRYPLYTKITVDIGTPS |
| 6 | | Human Stem Region of β(1,4)galactosyl-transferase | RDLSRLPQLVGVSTPLQGGSNSAAAIGQSSGD LRTGGARPPPPLGASSQPRPGGDSSPVVDSGP GPASNLTSVPVPHTTALSLPACPEESPLLVGP MLIEFNMPVDLELVAKQ |
| 7 | | Bovine Stem Region of β(1,4)galactosyl-transferase | RDLRRLPQLVGVHPPLQGSSHGAAAIGQPSG ELRLRGVAPPPPLQNSSKPRSRAPSNLDAYSH PGPGPGPGSNLTSAPVPSTTTR |
| 8 | | Human Catalytic Domain of | SLPACPEESPLLVGPMLIEFNMPVDLELVAKQ NPNVKMGGRYAPRDCVSPHKVAIIIPFRNRQE |

TABLE I-continued

Exemplary Amino Acid Sequences

| SEQ ID NO | Accession Number | Description | Amino Acid Sequence |
|---|---|---|---|
| | | β(1,4)galactosyl-transferase | HLKYWLYYLHPVLQRQQLDYGIYVINQAGD TIFNRAKLLNVGFQEALKDYDYTCFVFSDVD LIPMNDHNAYRCFSQPRRISVAMDKFGFSLP YVQYFGGVSASSKQQFLTINGFPNNYWGWG GEDDDIFNRLVFRGMSISRPNAVVGTCRMIR HSRDKKNEPNPQRFDRIAHTKETMLSDGLNS LTYQVLDVQRYPLYTQITVDIGTPS |
| 9 | | Bovine Catalytic Domain of β(1,4)galactosyl-transferase | SLTACPEESPLLVGPMLIEFNIPVDLKLIEQQN PKVKLGGRYTPMDCISPHKVAIIILFRNRQEH LKYWLYYLHPMVQRQQLDYGIYVINQAGES MFNRAKLLNVGFKEALKDYDYNCFVFSDVD LIPMNDHNTYRCFSQPRHISVAMDKFGFSLPY VQYFGGVSALSKQQFLSINGFPNNYWGWGG EDDDIYNRLAFRGMSVSRPNAVIGKCRMIRH SRDKKNEPNPQRFDRIAHTKETMLSDGLNSL TYMVLEVQRYPLYTKITVDIGTPS |

TABLE II

Exemplary Nucleic Acid Sequence

| SEQ ID NO | Accession Number | Description | Nucleic Acid Sequence |
|---|---|---|---|
| 10 | D29805 | Human β(1,4) galactosyl-transferase | ATGAGGCTTCGGGAGCCGCTCCTGAGCCGGA GCGCCGCGATGCCAGGCGCGTCCCTACAGCG GGCCTGCCGCCTGCTCGTGGCCGTCTGCGCTC TGCACCTTGGCGTCACCCTCGTTTACTACCTG GCTGGCCGCGACCTGAGCCGCCTGCCCCAAC TGGTCGGAGTCTCCACACCGCTGCAGGGCGG GTCGAACAGTGCCGCCGCCATCGGGCAGTCC TCCGGGGACCTCCGGACCGGAGGGGCCCGGC CGCCGCCTCCTCTAGGCGCCTCCTCCCAGCCG CGCCCGGGTGGCGACTCCAGCCCAGTCGTGG ATTCTGGCCCTGGCCCCGCTAGCAACTTGACC TCGGTCCCAGTGCCCCACACCACCGCACTGTC GCTGCCCGCCTGCCCTGAGGAGTCCCCGCTG CTTGTGGGCCCCATGCTGATTGAGTTTAACAT GCCTGTGGACCTGGAGCTCGTGGCAAAGCAG AACCCAAATGTGAAGATGGGCGGCCGCTATG CCCCCAGGGACTGCGTCTCTCCTCACAAGGT GGCCATCATCATTCCATTCCGCAACCGGCAG GAGCACCTCAAGTACTGGCTATATTATTTGCA CCCAGTCCTGCAGCGCCAGCAGCTGGACTAT GGCATCTATGTTATCAACCAGGCGGGAGACA CTATATTCAATCGTGCTAAGCTCCTCAATGTT GGCTTTCAAGAAGCCTTGAAGGACTATGACT ACACCTGCTTTGTGTTTAGTGACGTGGACCTC ATTCCAATGAATGATCATAATGCGTACAGGT GTTTTTCACAGCCACGGCACATTTCCGTTGCA ATGGATAAGTTTGGATTCAGCCTACCTTATGT TCAGTATTTTGGAGGTGTCTCTGCTTCAAGTA |

TABLE II-continued

Exemplary Nucleic Acid Sequence

| SEQ ID NO | Accession Number | Description | Nucleic Acid Sequence |
|---|---|---|---|
| | | | AACAACAGTTTCTAACCATCAATGGATTTCCT |
| | | | AATAATTATTGGGGCTGGGGAGGAGAAGATG |
| | | | ATGACATTTTTAACAGATTAGTTTTTAGAGGC |
| | | | ATGTCTATATCTCGCCCAAATGCTGTGGTCGG |
| | | | GACGTGTCGCATGATCCGCCACTCAAGAGAC |
| | | | AAGAAAAATGAACCCAATCCTCAGAGGTTTG |
| | | | ACCGAATTGCACACACAAAGGAGACAATGCT |
| | | | CTCTGATGGTTTGAACTCACTCACCTACCAGG |
| | | | TGCTGGATGTACAGAGATACCCATTGTATAC |
| | | | CCAAATCACAGTGGACATCGGGACACCGAGC |
| | | | TAG |

EXAMPLE I

General Expression, Mutagenesis, Folding, and Purification of Catalytic Domains of Bovine β(1,4)-galactosyltransferase I Materials and Methods Bacterial growth and plasmid transformations were performed using standard procedures (Ausubel et al., *Current Protocols in Molecular Biology*, Greene Publishing Associates and Wiley-Interscience, New York (1987)). The plasmid pEGT-d129, which encodes the catalytic domain (residues 130-402) of bovine β(1,4)-galactosyltransferase I, was used for mutation. Site-directed mutagenesis was performed using a CLONTECH site-directed mutagenesis transformer kit. The transformation mixture contained the template pEGT-d129, a selection primer, and a mutagenic primer for creation of a desired mutant. Mutants were screened for the incorporated mutations by looking for changes in restriction enzyme digestion patterns and confirmed by DNA sequencing. The positive clones were transformed into B834(DE3)pLysS cells. The primers were synthesized by the Molecular Technology Laboratory, NCI-Frederick.

The expression and purification of the inclusion bodies were carried out as described previously (Ausubel et al., *Current Protocols in Molecular Biology*, Greene Publishing Associates and Wiley-Interscience, New York (1987)). The inclusion bodies were S-sulfonated by dissolving in 5 M GdnHCl, 0.3 M sodium sulfite, and the addition of di-sodium 2-nitro-5-thiosulfobenzoate to a final concentration of 5 mM. The sulfonated protein was precipitated by dilution with water, and the precipitate was washed thoroughly.

The sulfonated protein was re-dissolved in 5 M GdnHCl to a protein concentration of 1 mg/ml (1.9-2.0 optical density at 275 nm). The protein solution was diluted 10-fold, in 10 portions, in a folding solution to give a final concentration of 100 μg/ml β(1,4)-galactosyltransferase I, 0.5 M GdnHCl, 50 mM Tris-HCl, 5 mM EDTA, 4 mM cysteamine, and 2 mM cystamine, pH 8.0 at 4° C. It was left at 4° C. for 48 h to allow the protein to fold and then dialyzed against 3×4 liters of water containing 50 mM Tris-HCl, pH 8.0, 5 mM EDTA, 4 mM cysteamine, and 2 mM cystamine at 4° C. to remove GdnHCl. Any protein that precipitated during dialysis was removed by centrifugation, and the supernatant was concentrated. Typically, when 100 mg of sulfonated protein was folded in a 1-liter folding solution, it yields 2-5 and 10-12 mg of the active, soluble, and pure wild-type β(1,4)-galactosyltransferase I catalytic domain, or mutant thereof. The folded proteins were purified further on an LA-agarose column (Sigma). The final, purified protein had a specific activity that was slightly higher than that of purified milk β(1,4)-galactosyltransferase I.

Site-directed Mutagenesis of amino acid position 289 of the bovine β(1,4)-galactosyltransferase I: Site-directed mutagenesis was performed using the PCR method. Construction of the mutants was done using plasmid pEGT-d129 as the template; this contains a BamH1/EcoRI fragment inserted into pEGT23a vector, coding for the residues 130-402 of bovine β(1,4)-galactosyltransferase I, and has a Cys-342 to Thr mutation.

The mutation primers corresponding to the upper DNA strand are: Y289L, 5'-CCTTACGTGCAATTGTTTGGAG-GTGTCTCTGCTCTAAGTAAA-3'(SEQ ID NO: 11) and 5'-GACACCTCCAAACAATTGCACGTAAGG-TAGGCTAAA-3' (SEQ ID NO: 12); Y289I, 5'-CTACCT-TACGTGCAGATCTTTGGAGGTGTCTCTGCTCTAAG-3' (SEQ ID NO: 13) and 5'-GACACCTCCAAAGATCTGCACGTAAGG-TAGGCTAATCCAA-3' (SEQ ID NO: 14); Y289N, 5'-GGATTAGCCTACCATATGTGCA-GAATTTTGGAGGTGTCTCT-3' (SEQ ID NO: 15) and 5'-AGAGACACCTCCAAAATTCTGCA-CATCTGGTAGGCTAAATCC-3' (SEQ ID NO: 16). Typically, the entire Gal-T1 DNA was PCR-amplified as two fragments using the terminal cloning primers and two mutagenesis primers. The fragments were then cut with the restriction enzymes MfeI, BglII, and NdeI for Y289L, Y286I, and Y286N mutants, respectively, and ligated. The full Gal-T1 DNA with the mutation was amplified from the ligation mixture using the cloning primers and then inserted into the pET28a vector. Mutants were screened for the incorporated mutations, based on alterations in the restriction enzyme digestion patterns, and then sequenced. The positive clones were transformed into B834(DES)pLys8 cells as described previously (Ramakrishnan et al., *J. Biol. Chem.*, 270, 87665-376717 (2001)). The mutant proteins were expressed and purified according to the published method (Ramakrishnan et al., *J. Biol. Chem.*, 270, 87665-376717 (2001)).

Gal-T and GalNAc-T Enzyme Assays: The protein concentrations were measured using the Bio-Rad protein assay kit, based on the method of Bradford and further verified on SDS gel. An in vitro assay procedure for the Gal-T1 has been reported previously (Ramakrishnan et al., *J. Biol. Chem.*, 270, 87665-376717 (2001)). The activities were measured using UDP-Gal or UDP-GalNAc as sugar nucleotide donors, and GlcNAc and Glc as the acceptor sugars. For the specific activity measurements, a 100-μl incubation mixture containing 50 mM β-benzyl-GlcNAc, 10 mM MnCl$_2$, 10 mM Tris-HCl, pH 8.0, 500 μM UDP-Gal or UDP-GalNAc, 20 ng of Gal-T1, and 0.5 μCi of [$^3$H]UDP-Gal or [$^3$H]UDP-GalNAc was used for each Gal-T or GalNAc-T reaction. The incubation was carried out at 37° C. for 10 min. The reaction was terminated by adding 200 μl of cold 50 mM EDTA, and the mixture was passed through a 0.5-ml bed volume column of AG1-X8 cation resin (Bio-Rad) to remove any unreacted [$^3$H]UDP-Gal or [$^3$H]UDP-GalNAc. The column was washed successfully with 300, 400, and 500 μl of water, and the column flow-through was diluted with Biosafe scintillation fluid; radioactivity was measured with a Beckman counter. A reaction without the acceptor sugar was used as a control. A similar assay was carried out to measure the GalNAc-T activity with Glc and other acceptors in the presence of 50 μM bovine LA (Sigma).

Studies for Determining the Kinetic Constants: The true $K_m$ of the donor ($K_A$) and of the acceptor ($K_B$), the dissociation constant of the donor, $K_{i(a)}$, and $k_{cat}$ were obtained using two-substrate analyses and the primary plots of five concentrations of donor (UDP-Gal or UDP-GalNAc) and five concentrations of acceptor, and the corresponding secondary plots of the intercepts and slopes. Initial rate conditions were linear with respect to time. A suitable range of donor and acceptor concentrations were chosen, which allowed an accurate Michaelis-Menten plot to be derived. The data were also analyzed for a general two-substrate system using the following equations (Zhang et al., Glycobiology, 9:815-822 (1999)) with the software EnzFitter, a Biosoft nonlinear curve-fitting program for Windows.

$$v = \frac{V_{\max}[A][B]}{K_{i(a)}K_B + K_A[A] + K_B[B] + [A][B]} \quad \text{Equation 1}$$

$$v = \frac{V_{\max}[A][B]}{K_A[A] + K_B[B] + [A][B]} \quad \text{Equation 2}$$

Here v is the initial velocity and the rate equation for sequential symmetrical initial velocity pattern associated with Equation 1, an ordered or random equilibrium mechanism in which substrate A dissociates well from the E-S complex with a dissociation constant of $K_{i(a)}$. Equation 2 is for asymmetric initial velocity pattern for a double displacement or "ping-pong" mechanism. The kinetic parameters $K_A$, $K_B$, $K_{i(a)}$, and $V_{max}$, were obtained from the fitted curves using the above rate equations. The graphical method and EnzFitter program gave very similar kinetic parameters. In the N-acetylgalactosamine transferase (GalNAc-T) assay, the maximum substrate concentrations used for UDP-GalNAc and GlcNAc were 1 and 200 mM, respectively. However, in the galactose transferase (Gal-T) assay, because of the limited solubility of GlcNAc in water, the concentration of GlcNAc was limited to no more than 400 mM (which is 2-fold higher than its $K_m$ value), whereas up to 300 μM UDP-Gal were used.

$^1$H NMR Spectroscopy of the Products of GalNAc-T Activity: The reaction was carried out in a total volume of 1 ml that contained 100 μg of Y289L mutant plus 10 mM each triethanolamine-HCl, pH 8.0, UDP-GalNAc, GlcNAc, and $MnCl_2$ at 37° C. for 48 h. The mixture was first passed through a 1-ml Chelex 100 column and then through a 1-ml cationic column containing AG 1-X8 resin (200-400-mesh). The disaccharide product in the flow-through from 4 bed volumes was pooled and freeze-dried. The product was finally dissolved in 400 μl of $D_2O$, and its $^1$H NMR spectrum was obtained in a 400-MHz NMR spectrometer. All the NMR spectra were recorded in the Analytical Chemistry Laboratory, NCI-Frederick (Frederick, Md.).

Results

Figure 1B:
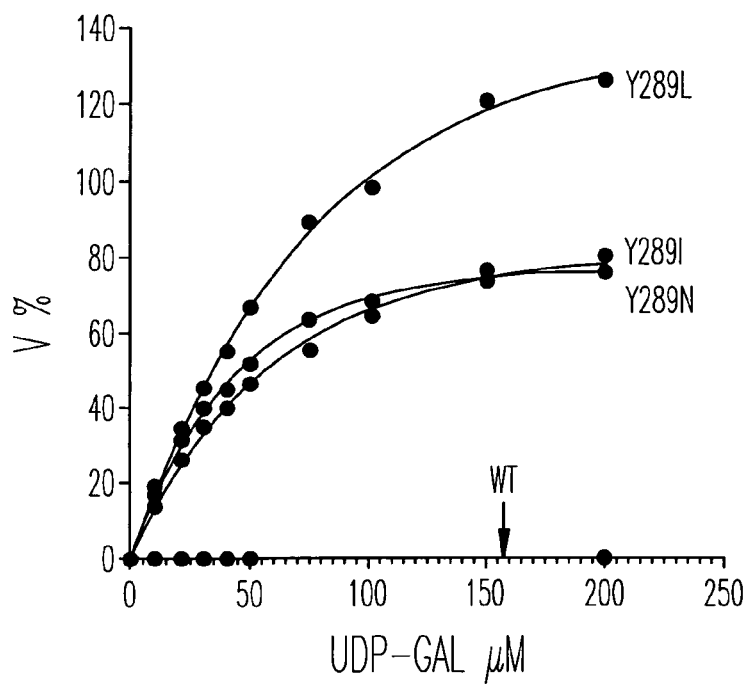
Figure 2:
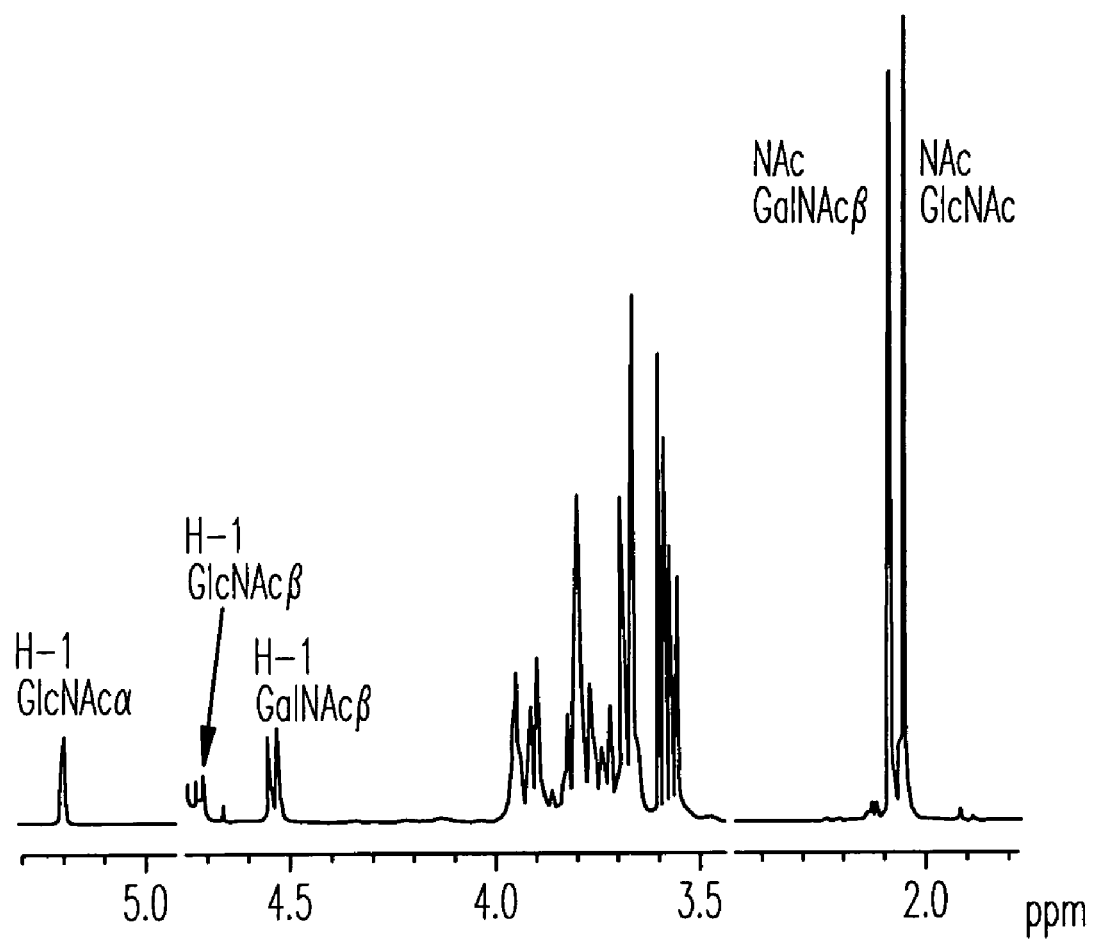
FIG. 2 illustrates the partial $^1$H NMR spectrum of the disaccharide (LacdiNAc) product from the GalNAc-T reaction with GlcNAc as the acceptor. The signal for the GalNAc anomeric proton is at δ 4.58 ppm and for the GlcNAc anomeric proton corresponding to an α and β conformer is at δ 5.2 and 4.7 ppm. The signals from the acetyl group of each sugar moiety are at δ 2.05 and 2.08 ppm.

Comparison of Gal-T and GalNAc-T Catalytic Activities of Wild-type and Gal-T1 Mutants: The mutants Y289L, Y289N, and Y289I exhibited both galactose transferase and N-acetylgalactosyltransferase activities (Table III and FIG. 1). The mutants Y289L and Y289N exhibited equally strong galactose transferase and N-acetylgalactosyltransferase activities. The specific N-acetylgalactosyltransferase activity of the mutant Y289I at the substrate concentration used was half that of Y289L (Table III). The Y289I mutant exhibited a slightly weaker affinity to UDP-GalNAc (FIG. 1). The Asn substitution exhibited GalNAc-T activity as well as the Leu substitution. Wild-type-Gal-T1 exhibits a very low glucosyltranferase activity, but no N-acetylglucosaminyltransferase activity (Berliner and Robinson, Biochemistry, 21:6840-68433 (1982); Palmin and Hindaganl, Glycobiology, 1:205-209 (1991); Ramakrishnan et al., J. Biol. Chem., 270:87665-37671(2001)). On the contrary, the mutants exhibited reasonable N-acetylglucosaminyltransferase activity (Table III) where they transfer N-acetylglucosamine from UDP-N-acetylglucosamine to the acceptor N-acetylglucosamine but do not exhibit glucosyltranferase activity. In this N-acetylglucosaminyltransferase activity the initial product, the disaccharide GlcNAc β1,4-GlcNAc, itself is an acceptor for the enzyme, thus producing tri- and longer chain saccharides.

TABLE III

Specific activities of the catalytic domain of Gal-T1 (residues 130-402) with the C342T mutation and the Tyr-289 mutants

| Enzyme | UDP-galactose → GlcNAc Gal-T activity pmol/min/ng | UDP-GalNAc → GlcNAc GalNAc-T activity pmol/min/ng | UDP-GlcNAc → GlcNAc GlcNAc-T activity pmol/min/ng |
|---|---|---|---|
| C342T | 11.8 | 0.1 | 0 |
| Y289L_C342T | 16.2 | 27.3 | 8.2 |
| Y289I_C342T | 8.8 | 14.7 | 6.2 |

Reactions were performed under saturating conditions of all substrates (assay conditions are described herein). In these reactions, the concentration for the donors was 500 μM and the acceptor β-benzyl-GlcNAc was 25 mM. In the Gal-T reaction of C342T, the acceptor concentration was 10 mM, because at 25 mM it showed inhibition. Because Y289N rapidly undergoes denaturization, reliable data could not be obtained.

Because the Y289L variant of Gal-T1 exhibits both Gal-T and GalNAc-T enzyme activities with equal efficiencies, double substrate kinetic studies were carried out to determine the kinetic constants for both donor and acceptor molecules. The kinetic data from both reactions fit best to Equation 2, with a zero $K_{i(a)}$ value, describing an asymmetric initial velocity pattern for a double-displacement or "ping-pong" mechanism. The Y289L mutant in the Gal-T reaction showed nearly a 20-fold higher $K_m$ for the acceptor than the wild-type Gal-T1 (Table IV). The catalytic constant ($k_{cat}$) in the Gal-T1 reaction is comparable with the wild type, but it is nearly 3-5-fold higher in the GalNAc reaction (Table IV).

TABLE IV

Kinetic parameters for the donor and the acceptor substrates by Y289L_C342T mutant in the Gal-T and the GalNAc-T catalytic reactions

| Mutant | Gal-T UDP-galactose → GlcNAc | | | GalNAc-T UDP-N-acetylgalactosamine → GlcNAc | | |
|---|---|---|---|---|---|---|
| | $K_A$ μM | $K_B$ MM | $K_{cat.}$ | $K_A$ μM | $K_B$ mM | $K_{cat.}$ |
| C342T | 98 (6) | 11 (1) | 14 | ND | ND | ND |
| Y289L_C342T | 75 (1) | 198 (1) | 8.5 | 854 (8) | 51 (1) | 4.0 |

ND, not determined

Figure 4:
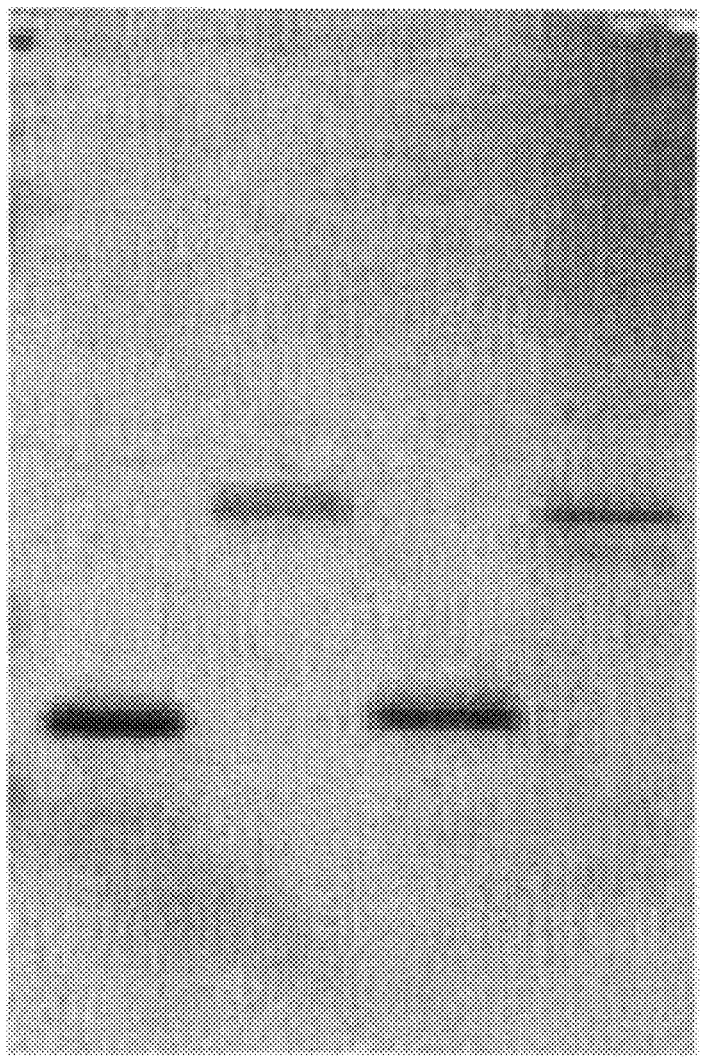
FIG. 4 shows an SDS-PAGE analysis of the recombinant CD and SRCD proteins of β4Gal-T produced in E. coli. Purified inclusion bodies were analyzed on 14% SDS-PAGE. Lane 1, bovine CDβ4Gal-T1; Lane 2, bovine SRCD β4Gal-T1; Lane 3, human CDβ4Gal-T1; and Lane 4, human SRCDβ4Gal-T1.

Because the Y289L mutant exhibits equally high GalNAc-T activity as it does Gal-T activity, the disaccharide product from this reaction was purified and analyzed by $^1$H NMR spectroscopy (FIG. 4). The NMR results demonstrated that the mutant Y289L transfers GalNAc from UDP-GalNAc to GlcNAc, forming a β1-4 linkage between GalNAc and GlcNAc.

A Point Mutation in the Codon for Amino Acid 289 Can Convert the Enzyme with Dual Property: In humans, the β4Gal-T family has seven members (Gal-T1 to -T7), each with high sequence identity within their catalytic domain (Lo et al., *Glycobiology*, 8:517-526 (1998); Nomura et al., *J. Biol. Chem.*, 273:13570-13577 (1998)). These family members transfer Gal from UDP-Gal to different sugar acceptors. For example, Gal-T6 transfers Gal to Glc of Glc-ceramide, whereas Gal-T7 transfers Gal to xylose (Nomura et al., *J. Biol. Chem.*, 273:13570-13577 (1998)). Among these seven members, four members, Gal-T1 to Gal-T4, have a Tyr residue at position 287 (which corresponds to Tyr-289 in bovine Gal-T1), whereas Gal-T5 and Gal-T6 have a Phe residue.

TABLE V

Codon usage for the amino acid at position 289 among the Gal-T1 family members

| Enzyme | Codon | Amino acid at position 289 |
|---|---|---|
| Bovine Gal-T1 | TAT | Tyr |
| Human Gal-T1 | TAT | Tyr |
| Human Gal-T2 | TAC | Tyr |
| Human Gal-T3 | TAC | Tyr |
| Human Gal-T4 | TAT | Tyr |
| Human Gal-T5 | TTT | Phe |
| Human Gal-T6 | TTC | Phe |
| Human Gal-T7 | TAC | Tyr |

In human Gal-T1, the corresponding amino acid is at position 287. The second and third nucleotides of the codon show variations among the family members, while strictly conserving the first nucleotide. Mutation of the first nucleotide of the codon (shown in bold) to either A or C would result in a Leu or Asn residue instead of Tyr, and such a mutant would exhibit dual enzymatic activities.

Role of α-Lactalbumin (LA) in the GalNAc-T Activity of the wt-Gal-T1 and the Y289L Mutant: LA enhances the transfer of GalNAc from UDP-GalNAc to GlcNAc by Gal-T1 with ~0.1% of its Gal-T efficiency, a situation similar to glucosyltransferase activity (Glc-T) of Gal-T1, where LA increases this activity from 0.3 to 10% (Ramakrishnan et al., *J. Biol. Chem.*, 270:87665-37671 (2001)). LA plays a kinetics role in stimulating Gal-T1 to transfer Glc from the UDP-Glc to GlcNAc (Ramakrishnan et al., *J. Biol. Chem.*, 270:87665-37671 (2001); Ramakrishnan et al., *Biochem Biophys. Res. Commun.*, 291:1113-1118 (2002)). The activity is enhanced by approximately 1%. This level of activity was determined using the donor concentration of the unlabeled UDP-sugar, and only a small amount of $^3$H-labeled UDP-sugar. Use of this protocol allowed for accurate calculation based on the amount of unlabeled UDP-sugar used.

Unlike wt-Gal-T1, where LA stimulates the transfer of GalNAc only to GlcNAc and not to Glc (Do et al., *Biol. Chem.*, 276:18447-18451 (1995)), the Tyr-289 mutants (Y289L, Y289N, and Y289I) in the presence of LA transfer GalNAc preferably to Glc rather than to GlcNAc. This property is quite similar to LS activity in which the wt-Gal-T1 in the presence of LA transfers Gal to Glc instead to GlcNAc (Table VI). Furthermore, like wt-Gal-T1, these mutants also transfer Gal to Glc in the presence of LA. For example, the N-acetylgalactosaminyltransferase activity in the bovine mammary gland extracts with a similar catalytic property has been identified (Van den Nieuwenhof et al., *FEBS Lett.*, 459: 377-380 (1999)). This enzyme also transfers GalNAc from UDP-GalNAc to GlcNAc in the absence of LA, whereas in the presence of LA it transfers GalNAc to Glc instead to GlcNAc.

TABLE VI

GalNAc-T catalytic activity of Y289L mutant in the absence and the presence of LA on various acceptor substrates

| | GalNAc-T activity | |
|---|---|---|
| | −LA | +LA |
| Acceptor | pmol/min/ng | |
| GlcNAc | 31.3 | 3.3 |
| Glc | 2.6 | 34.8 |
| Glucosamine | 1.8 | 5.0 |

Assays were carries out at 37° C. using 500 μM UDP-GalNAc for 10 minutes. In all the measurements, the acceptor concentration was 100 mM and the LA concentration was 55 μM.

It is shown herein that the Tyr-289 mutants of Gal-T1 exhibit as high GalNAc-T activity as Gal-T activity, as well as GlcNAc-T activity. In the human Gal-T family members, the Tyr/Phe residue at 287 (or in bovine Tyr-289) is important for determining the donor sugar specificity of the enzyme.

EXAMPLE II

General Expression, Mutagenesis, Folding, and Purification of Catalytic Domains of β(1,4)-galactosyltransferase I Enzymes Having an N-Terminal Stem Region Materials and Methods Restriction endonucleases and DNA-modifying enzymes were from New England Biolabs (Beverly, Mass.). Oligonucleotide primers were synthesized by the Recombinant DNA Facility at NCI-Frederick. The plasmid mini preparation kit was from Qiagen (Santa Clarita, Calif.). Ampicillin, UDP-Gal and UDP-agarose were from Sigma Chemical Co, MO. pET23a vector and BL21 (λDE3)/pLysS competent cells were from Novagen (Madison, Wis.). E. coli XL2-Blue ultracompetent cells were from Stratagene (La Jolla, Calif.). AG1-X8 resin, chloride form, 200-400 mesh was from Bio-Rad (Hercules, Calif.). Taq DNA polymerase and PCR nucleotide mixes were obtained from Boehringer Mannheim.

Cloning of Bovine and Human Stem-CD Clones of β1,4-galactosyltransferase:

Two sets of oligonucleotide primers with unique restriction sites added at the 5' (SR) and 3' (CD) ends were synthesized based upon the bovine β4Gal-T1 and human β4Gal-T1 cDNA sequence (shown in FIGS. 3A and 3B). A full-length bovine cDNA clone encoding β4Gal-T1 was used for site-directed mutagenesis (Boeggeman et al., *Protein Eng.*, 6:779-785 (1993)). In the stem region of bovine β4Gal-T1 Ser96 was mutated to Ala96 (described below). The mutated full-length cDNA template was amplified by the polymerase chain reaction (PCR), using the following primer pair to generate SRCDβ4Gal-T1:

(SR)                                                    (SEQ ID NO: 17)
5'-CGCGGATCCCGCGACCTAAGACGCCTGCCTCAGCTGGTC-3'
and (CD)                                                    (SEQ ID NO: 18)
5'-TGGAATTCCTAGCTCGGCGTCCCGATGTCCACTGTGAT-3'.

Human placental QUICK-Clone cDNA (Lot # 9020891) was obtained from Clontech and used as the template for PCR. To amplify human β4Gal-T1 the following PCR primers were used:

(SR)                                                    (SEQ ID NO: 19)
5'-CGCGGATCCCGCGACCTGAGCCGCCTGCCCCAACTGGTC-3'
and (CD)                                                    (SEQ ID NO: 20)
5'-CCGGAATTCCTACTAGCTCGGTGTCCCGATGTCCACTGT-3'.

The primer pairs amplified the cDNA region that has both the stem and catalytic domain, and were designed to generate DNA fragments containing a Bam HI (SR) and Eco RI (CD) (underlined) at the 5' and 3'-ends of the inserts, respectively. The PCR products were purified using a QIAquick PCR purification kit and the purified fragments were digested with Bam HI and Eco RI to generate the cohesive ends. The expression constructs were obtained after ligating the digested and gel-purified PCR fragments into the Bam HI and Eco RI-digested pET23a vector (Novagen, Madison, Wis.) and transformed into XL2-ultracompetent cells. Identities of the clones were confirmed by DNA sequence.

Mutation of the stem region of bovine β4Gal-T1 to inhibit proteolysis: The wild-type bovine SRCDβ4Gal-T1, which has Ser at position 96, was expressed in E. coli. Its sequence is shown in FIG. 3A. The recombinant wild-type protein folded and purified from inclusion bodies, as described below, was cleaved within the SR region, over a short period of time. The cleaved protein on SDS-PAGE shows a single band of molecular mass of 34.9 kDa. The protein was electroblotted to polyvinylidene difluoride membrane, and the N-terminal sequence of the cleaved fragment was determined by Edman degradation at the Protein Chemistry Laboratory, NCI-Frederick. The N-terminal sequence of the fragment was determined as SRAPSNLD (SEQ ID NO: 21). This corresponds to the cleavage at Ser96 within the sequence region KPR$^{96}$SRAPSNLD (SEQ ID NO: 22). To prevent this proteolytic digestion within the stem region, we now constructed a mutant substituting Ala in place of Ser96. This prevented the cleavage within the stem region of bovine β4Gal-T1 keeping the recombinant protein intact for a long period of time. Even though, the experimental results described in this study are with the mutant bovine S96A-SRCDβ4Gal-T1 (FIG. 3A), for the sake of convenience in abbreviation this protein is simply referred to as bovine SRCDβ4Gal-T1. The human SRCDβ4Gal-T1 also gets cleaved within the stem region, at Val53 in the sequence QLV$^{53}$GVSTPLQ (SEQ ID NO: 23), but only after long periods of time. Since this clone showed more stability than the bovine β4Gal-T1, it was not mutated and used as such for subsequent analysis.

Protein expression in E. coli and inclusion body isolation: For protein expression BL21 (λDE3)/pLysS-competent cells were transformed with the pET vector derivatives according to the manufacturer's protocols. The transformed cells were grown in LB broth containing 50 μg.ml$^{-1}$ ampicillin to an OD600 nm of ~0.7, followed by induction with 0.4 mM IPTG. Cultures were harvested after 3-4 hours by centrifugation at 2000×g for 20 min. The inclusion bodies were isolated and solubilized as described (Boeggeman et al., *Protein Eng.*, 6:779-785 (1993)). From a liter of induced bacterial culture, the yield is generally 80 to 100 mg of purified inclusion bodies. Novex gels were used for SDS-PAGE analysis and the protein bands were visualized with Coomassie blue. Protein concentrations were measured with the Bio-Rad protein dye reagent with bovine serum albumin as the standard.

In vitro folding of proteins from inclusion bodies: A protocol utilizing oxido-shuffling agents within the renaturation buffer was used to generate active recombinant β4Gal-T1 from the inclusion bodies (Boeggeman et al., *Protein Eng.*, 6:779-785 (1993)). After renaturation and subsequent dialysis of the solution, a portion of the folded protein precipitated in the form of insoluble aggregates. To increase the yields of native proteins, the inclusion bodies were sulfonated as previously described (Boeggeman et al., *Glycobiology*, 12:395-407 (2002)). The sulphonated proteins were dissolved in 5 M guanidine-HCl, to a protein concentration of 1 mg/ml, with an OD275 mm of 1.9 to 2.0. The protein solution was then diluted 10-fold in small aliquots in a renaturation solution to give a final protein concentration of 100 μg/ml, in 50 mM Tris-HCl pH 8.0, 5 mM EDTA, 0.5 M guanidine-HCl, 8 mM cysteamine and 4 mM cystamine. The protein was allowed to renature for 48 hrs at 4° C. and then dialyzed. The precipitate was removed by centrifugation at 5000 rpm and the supernatant concentrated using ultrafiltration membranes (Amicon, Inc., Beverly, Mass., USA).

Improving the folding conditions: In recent years factorial folding screens (Rudolph and Lilie, *FASEB J.,* 10:40-56 (1996); Chen and Gouaux, *Proc. Natl. Acad. Sci.,* 94:13431-13436 (1997); Armstrong et al., *Prot. Sci.,* 8:1475-1483 (1999)) have been developed for examining the folding efficiencies of proteins from inclusion bodies. To improve the in vitro folding efficiency, 8 different folding conditions similar to the formulations described in the FoldIt Screen kit (Hampton Research, Calif.) with certain modifications were tested. Condition I: 50 mM Tris-HCl pH 8.0, 5 mM EDTA, 0.5 M guanidine-HCl, 8 mM cysteamine and 4 mM cystamine. Condition II: 55 Mes pH 6.5, 10.56 mM NaCl, 0.44 mM KCl, 2.2 mM $MgCl_2$, 2.2 mM $CaCl_2$, 0.5 M guanidine-HCl. Condition III: similar to condition II with respect to the buffer, pH, chaotrope and salt condition, but it had 0.055% PEG-4000, 1.1 mM EDTA, 0.44 M sucrose and 0.55 M L-arginine. Condition IV: 55 mM Mes pH 6.5, 264 mM NaCl, 11 mM KCl, 0.055% PEG-4000, 0.5 M guanidine-HCl, 2.2 mM MgCl2, 2.2 mM $CaCl_2$ and 0.44 M sucrose. Condition V: 55 mM Tris pH 8.2, 10.56 mM NaCl, 0.44 mM KCl, 1.1 mM EDTA, 0.44 M sucrose. Conditions VI and VIII are similar except for the presence of redox agents. Condition VII: 55 mM Mes pH 6.5, 264 mM NaCl, 11 mM KCl, 1.1 mM EDTA, 0.5 M guanidine-HCl, and 0.55 M L-arginine. The buffers II through VII had 100 mM GSH and 10 mM GSSG. Conditions I and VIII, had 8 mM cysteamine and 4 mM cystamine. Condition VIII, gave the highest enzymatic activity, soluble and folded protein, was 50 mM Tris-HCl pH 8.0, 10.56 mM NaCl, 0.44 mM KCl, 2.2 mM MgCl2, 2.2 mM $CaCl_2$ 0.5 M guanidine-HCl, 8 mM cysteamine and 4 mM cystamine, 0.055% PEG-4000 and 0.55 M L-arginine.

β4Gal-T1 Enzyme Assays: The in vitro assay for β4Gal-T1 enzyme activity was performed as described (Boeggeman et al., *Glycobiology,* 12:395-407 (2002)). The $^3$H-labeled-UDP-Gal was used as sugar donor and GlcNAc as the sugar acceptor. A reaction without GlcNAc was used as a control. The fusion SRCDβ4Gal-T1 proteins showed the same enzymatic activities when compared to the wild-type recombinant β4Gal-T1 (amount of product formation/min/mol of protein).

Binding of recombinant proteins to UDP-affinity column: UDP-agarose was used to bind the active proteins at 4° C. Columns containing 1 ml bed volume of UDP-agarose were pre-equilibrated with 10 ml of 25 mM cacodylic buffer, pH 7.6, containing 25 mM MnCl2. The renatured protein solutions (0.5 mg) were adjusted to the pre-equilibration buffer conditions and applied to the columns. After loading the sample, the pass-through was re-cycled. It was then analyzed for the unbound protein by SDS-PAGE. The columns were washed 3× with 1-ml portions of equilibration buffer. The bound protein was eluted with the elution buffer consisting of 25 mM cacodylic buffer, pH 7.6, 25 mM EDTA and 1 M NaCl. Fractions of 0.5 ml were collected from the columns, and aliquots were analysed by SDS-PAGE. For enzymatic analysis the appropriate fractions were pooled and dialysed against 50 mM Tris-HCl pH 8.0 at 4° C.

Circular dichroism-spectroscopy: Far ultraviolet circular dichroism spectra of recombinant proteins was measured in a JASCO J-715 spectropolarimeter. The spectra for each sample was scanned at a speed of 100 nm/min. Far ultraviolet circular dichroism spectra were obtained from 190 to 250 nm at room temperature using a pathlength of 0.1 mm with a 1.0 nm bandwidth. Protein was dissolved in Tris-HCl pH 8.0 at concentrations of 0.5 mg/ml. Buffer blanks obtained in the same cuvette were subtracted to generate net spectra. Raw ellipticity data were transformed into molar residue ellipticity using the concentration values determined from optical ultraviolet absorbance measurements. No smoothing or data averaging was applied.

Results

Influence of the Stem Region (SR) Covalently Linked to the N-Termini of the Catalytic Domain (CD) of the β4Gal-T Family Members on the In Vitro Folding Efficiency of the Recombinant Proteins from Inclusion Bodies The catalytic domain of β4Gal-T1 (amino acid residues 130-402) (sequence in FIG. 3A, SEQ ID NO: 9) accumulated as an insoluble material within the inclusion body fraction upon expression in *E. coli*. Essentially all the proteins with the stem regions covalently linked to the N-termini of the catalytic domain (sequence in FIG. 3A, SEQ ID NO: 9) also accumulated in the insoluble inclusion body fraction. Contaminating proteins from the inclusion bodies were removed by washing the insoluble pellet several times with a buffer containing 25% sucrose as described herein. The yield of the purified inclusion bodies, varied with the protein that is being expressed (Table VII). The proteins produced a single protein band of expected molecular size on SDS-PAGE gel (FIG. 4). These insoluble inclusion bodies required 5 M guanidine HCl for solubilization.

Sulphonation of the inclusion bodies of CDβ4Gal-T1 prior to the in vitro folding step gave higher yields of final folded proteins. The yield of sulphonated protein from the purified inclusion bodies was generally half of the starting protein material (Table VII). Oxido-shuffling reagents were present during the renaturation step to regenerate the enzyme activity from all the recombinant sulphonated proteins. The recombinant proteins having the stem region fused at the N-termini of the catalytic domain (SRCD) remained soluble during the renaturation step in 0.5 M guanidine HCl and the oxido-shuffling agents. Upon subsequent dialysis of the SRCD-protein solutions, to remove the guanidine HCl, both the folded and misfolded molecules remained soluble as judged by SDS-PAGE analysis. In contrast, a majority of the misfolded protein molecules aggregated and precipitated in the protein solution containing only the CD. The recovery of soluble human and bovine SRCDβ4Gal-T1 is 3- to 9-fold higher than proteins having only the CD domain following refolding in the absence of PEG-4000 and L-arginine. (Table VIII).

TABLE VII

Yield of inclusion bodies and sulphonated proteins

| Recombinant Proteins | Inclusion body (mg)* | Amount of sulphonated protein recovered from inclusion bodies (mg)+ |
|---|---|---|
| Bovine CDβ4GalT-1 | 120 | 65 |
| Bovine SRCDβ4GalT-1 | 113 | 50 |
| Human CDβ4GalT-1 | 80 | 37 |
| Human SRCDβ4GalT-1 | 90 | 50 |

*Amount of inclusion bodies obtained from the pellet of one liter of IPTG induced bacterial culture.
+Amount of sulphonated protein was determined by SDS-PAGE and by protein estimation using the Bradford method (Bio Rad).

TABLE VIII

In vitro renaturation of the sulphonated inclusion bodies

| | −PEG/L-Arg⁺ | | +PEG/L-Arg⁺ | |
| --- | --- | --- | --- | --- |
| | CDβ4Gal-T1 mg (%)*^ | SRCDβ4Gal-T1 mg (%)*^ | CDβ4Gal-T1 mg (%)*^ | SRCDβ4Gal-T1 mg (%)*^ |
| Bovine | 2.7 (14) | 9.4 (47) | 8.3 (42) | 18.0 (90) |
| Human | 2.1 (11) | 19.0 (95) | 14.0 (69) | 20.0 (100) |

⁺20 mg of sulphonated proteins were folded in the buffer previously described that does not contain PEG-4000 and L-arginine (condition I) (Boeggeman, et al.). The proteins after the renaturation step were dialyzed, centrifuged and their concentration determined by SDS-PAGE and the Bradford method (BioRad)
*Percentage recovery of the soluble protein after in vitro folding of 20 mg of sulphonated β4Gal-T1
^The soluble renatured CDβ4Gal-T1 protein contains almost all folded molecules, whereas the soluble renatured SRCDβ4Gal-T1 contains misfolded proteins that are removed on UDP-agarose columns (see Table IX)

Figure 5A:
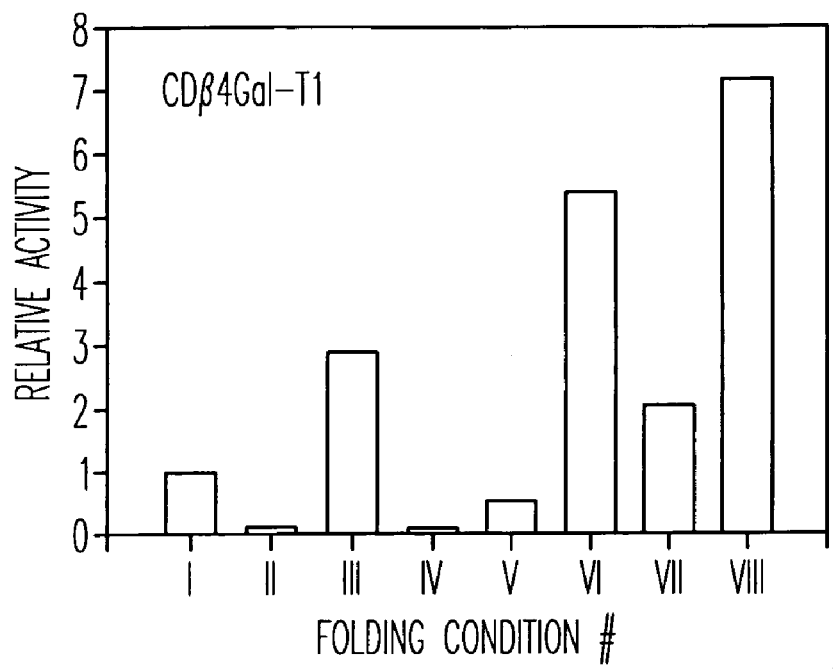
FIG. 5 shows folding of inclusion bodies under different renaturation conditions: the relative activities of CDβ4Gal-T1 and SRCDβ4Gal-T1. The relative activity was calculated with respect to the folding condition I. The largest amount of folded CDβ4Gal-T1 and SRCDβ4Gal-T1 was obtained under condition VIII. The enzyme activity under condition I for CDβ4Gal-T1 was 0.052 pmol/min/ng, and for SRCDβ4Gal-T1 0.09 pmol/min/ng of N-acetyllactosamine.
Figure 5B:
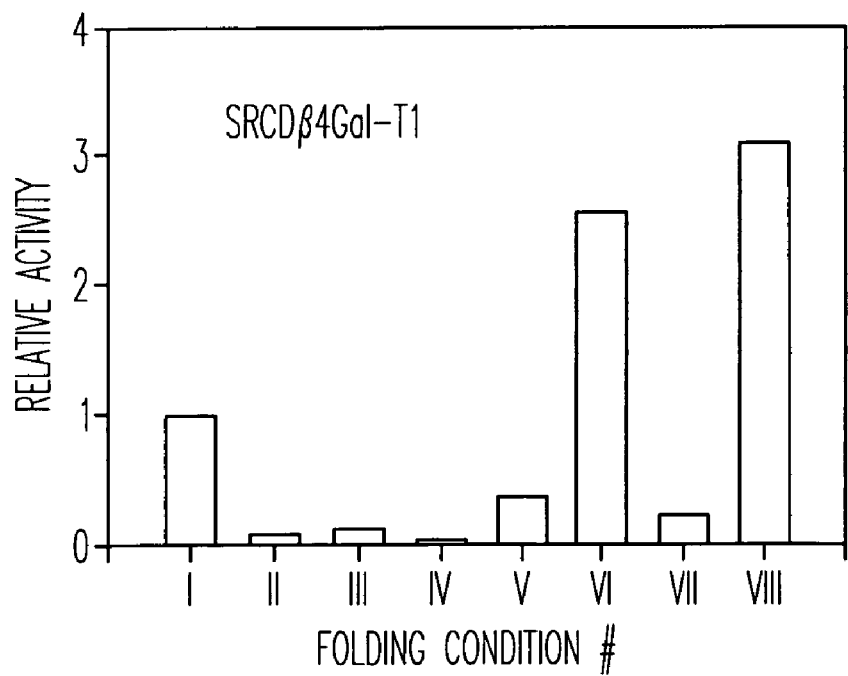

Renaturation conditions that increase the folding efficiency and specific activity of β4Gal-T1: After folding the bovine wild-type CDβ4Gal-T1 in a renaturation buffer I (described herein), the misfolded proteins precipitated out during subsequent dialysis. In an attempt to increase the amount of the folded native protein during the renaturation step, various folding conditions consisting of seven different solutions were tested. The results were compared to the yields obtained according to condition I (FIG. 5). The tested inclusion bodies were dissolved in 5 M guanidine HCl to a final protein concentration of 1 mg/ml. Aliquots of 50 μl of the protein solution were added to 950 μl of the folding buffers in an eppendorf tube, mixed gently and incubated at 4° C. for times ranging from 4 hours to overnight. The folding buffers varied, (conditions I to VIII as disclosed herein) with respect to: pH from 6.5 (in conditions II, III, IV and VII), to 8.0 (in conditions V, VI, and VIII); cations (in conditions II, IV, VI and VIII) and chelators (conditions I, III, V and VII). Conditions VI, VII and VIII had polar additives (L-arginine). Conditions IV and V had non-polar additives, such as sucrose. Condition III had both sucrose and L-arginine. Some buffers also had PEG-4000 (conditions III, IV, VI and VIII). The appropriate redox environment was created by the presence of 100 mM reduced (GSH) and 10 mM oxidized (GSSH) glutathione, except under conditions I and VIII which contained cysteamine (8 mM) and cystamine (4 mM).

After overnight incubation and dialysis against 1 mM Tris-HCl pH 8.0, samples were centrifuged and 5 μl of supernatant from each sample was tested for galactosyltransferase activity and compared with each other (FIG. 5). The results showed the highest activity under the buffer condition VI and VIII. Both of these had 0.55 M L-arginine and 0.055% PEG-4000 (FIG. 5). All folding conditions were tested in the presence of 30 mM lauryl maltoside, which appears to have a negative effect on the folding yields of the recombinant proteins, even in the presence of 0.55 M L-arginine and 0.055% PEG-4000. The inclusion of sucrose had an inhibitory effect (condition IV and V). No preference was observed for pH, salts, or cations within the conditions tested. The redox environment created by 8 mM cysteamine: 4 mM cystamine, (condition VIII), was preferred over 100 mM GSH: 10 mM GSSH (condition VI). Enzymatic assays (FIG. 5) revealed that the combination of L-arginine and PEG-4000 in condition VIII, increased the in vitro folding efficiency of the CD and SRCD proteins by about 7- and 3-fold, respectively, compared to condition I which did not contain PEG-4000 and L-arginine.

Figure 6:
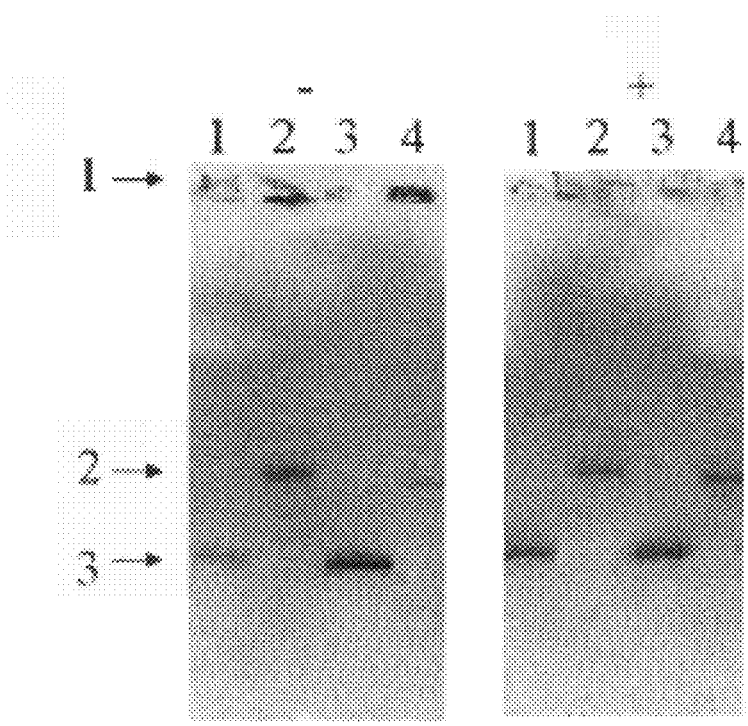
FIG. 6 shows analysis of the soluble proteins obtained after renaturation of inclusion bodies by SDS-PAGE electrophoresis. Under native conditions (−), (without boiling and in the absence of β-ME) and under denaturing conditions (+) (samples boiled in the presence of β-ME). Lane 1: bovine CDβ4Gal-T1; Lane 2: bovine SRCDβ4Gal-T1; Lane 3: human CDβ4Gal-T1; and Lane 4: human SRCDβ4Gal-T1. Under native conditions a portion of the soluble SRCD sample representing misfolded proteins does not enter the gel (arrow 1 in lanes 2 and 4).

Misfolded proteins in the renatured SRCDβ4Gal-T1: Renatured proteins were analyzed on SDS-PAGE gels under native and reducing conditions to determine whether the renatured SRCDβ4Gal-T1 proteins were natively folded or misfolded. Analyses under native conditions, in the absence of β-mercaptoethanol (βME) and without boiling the samples, revealed that both bovine and human soluble SRCDβ4Gal-T 1 proteins contained misfolded molecules that aggregated and remained at the top of the gel (FIG. 6 (−)). Under reducing conditions, using PME in the boiled samples, the misfolded molecules of both bovine and human soluble SRCDβ4Gal-T1 proteins did not appear on the top of the wells in SDS-PAGE and produced single protein bands of the expected sizes (35 kDa for bovine species and 34 kDa for human species) (FIG. 6 (+)).

Figure 7:
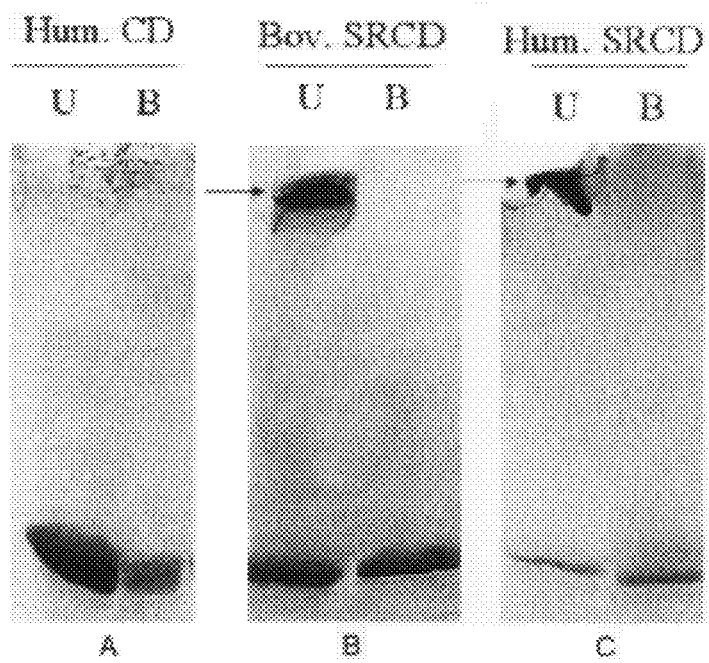
FIG. 7 illustrates binding and characterization of folded CDβ4Gal-T1 and SRCDβ4Gal-T1 on UDP-agarose columns. The purity of the proteins was judged using SDS-PAGE analysis under native conditions in the absence of βME and without boiling the samples. The protein sample before loading on the UDP-agarose column (U) and after eluting with 25 mM EDTA and 1M NaCl (B). Panel (A) shows the results with the human CDβ4Gal-T1 before and after passing through the UDP-agarose column, (bovine CDβ4Gal-T1 [not shown] behaves in the same way). Panel (B) shows the results with bovine SRCDβ4Gal-T1, and Panel (C) shows the results with human SRCDβ4Gal-T1. The arrows at the top of the lanes in panels B and C show the presence of soluble but misfolded proteins.

Binding of recombinant proteins to affinity columns: Folded and active CDβ4Gal-T1 obtained from inclusion bodies bound to, and was eluted from, a UDP-column with 25 mM EDTA and 1M NaCl. Thus, binding of soluble renatured CD and SRCDβ4Gal-T1 proteins to UDP-agarose columns was tested. Native SDS gel analyses of the soluble renatured CDβ4Gal-T1 protein, without PME and boiling, showed that all of the soluble renatured CD protein was natively folded. The renatured SRCDβ4Gal-T1 proteins were then applied to a UDP-agarose column. Nearly all of the renatured SRCDβ4Gal-T1 proteins bound to, and eluted from, the UDP-agarose column (FIG. 7). The specific enzymatic activity of the SRCDβ4Gal-T1 protein (product formation/min/ng protein) before and after being passed through the UDP-agarose column was measured to determine if the soluble protein fraction of the renatured SRCDβ4Gal-T1 protein contained properly folded molecules (FIG. 8). Also, the samples were analyzed in the absence of βME and without boiling. When condition I was used to fold bovine- and human-SRCD proteins (FIG. 8A), the folded molecules that eluted with 25 mM EDTA and 1 M NaCl, (FIG. 8A (+)) had 2- and 6-fold higher specific activities (FIG. 8A, crossed-hatched bars), respectively, when compared to the protein before loading onto the affinity column (FIG. 8A, black bars). The renatured human SRCDβ4Gal-T1 sample showed more misfolded proteins compared to bovine SRCDβ4Gal-T1 (FIG. 8A, bovine versus human black bars). In contrast, folding according to condition VIII, that contains PEG-4000 and L-arginine (FIG. 8B), increased properly folded human SRCD compared to condition I (FIG. 8B vs FIG. 8A, black bars, human SRCD). Protein eluted from the UDP-column under condition VIII (FIG. 8B, cross bar) had ~2-fold higher specific activity as compared to the proteins before being loaded on the affinity column (FIG. 8B, black bars). Although soluble, a portion of the protein in the SRCD samples is not folded to enable binding to UDP-agarose. The increased specific activity of the eluted proteins indicated the amount of misfolded molecules present in the sample before being bound to the UDP-agarose column. These results agreed with the observation that the misfolded proteins in the samples before being passed through the UDP-agarose columns also remained at the top of the wells in the SDS-PAGE gel (FIGS. 7B and C, lane U). The soluble bovine and human CDβ4Gal-T1 behaved the same way regardless of the buffer used for folding (condition I or VIII) (Table IX). The specific activity of bovine and human CDβ4Gal-T1 before and after binding on UDP-agarose columns did not change.

TABLE IX

Binding of in vitro folded β4Gal-T1 to UDP-agarose column

| | −PEG/L-Arg | | | | | +PEG/L-Arg | | | | |
|---|---|---|---|---|---|---|---|---|---|---|
| | CDβ4Gal-T1 | | SRCDβ4Gal-T1 | | | CDβ4Gal-T1 | | SRCDβ4Gal-T1 | | |
| % yield* | Input+ mg | Output mg | % yield* | Input+ mg | Output mg | Input+ mg | Output mg | % yield* | Input+ mg | Output mg | % yield* |
| Bovine (38) | 2.7 | 2.7 | (14) | 9.4 | 7.5 | 8.3 | 8.3 | (42) | 18.0 | 10.0 | (50) |
| Human (61) | 2.1 | 2.1 | (11) | 19.0 | 12.2 | 14.0 | 14.0 | (69) | 20.0 | 11.0 | (55) |

+The amount of soluble protein, recovered from 20 mg of sulphonated protein after in vitro folding, loaded on UDP-agarose columns.
*Percentage of final protein yield from 20 mg of sulphonated inclusion bodies after in vitro folding and passing through the UDP-agarose column. All of the soluble folded CDβ4Gal-T1 proteins bind to and elute from the UDP-agarose columns. On the other hand, the soluble folded SRCDβ4Gal-T1 fraction contains misfolded proteins that do not bind to the UDP-agarose column.

Circular dichroism-spectra of recombinant β4Gal-T1: Circular dichroism experiments were done with purified β4Gal-T 1 proteins to determine if the addition of the stem disturbed the overall secondary structure of β4Gal-T1. No significant differences in secondary structure relative to the wild-type CDβ4Gal-T1 were detected for the bovine or human proteins. All systems showed extrema of negative ellipticity between 250 and 200 nm. The circular dichroism-spectrum of the wild-type enzyme was highly reproducible and showed negative extrema at 208 and 220 nm indicative of α-helicity. There was a small change in ellipticity observed in the 200-210 nm region upon the addition of the stem in both bovine and human SRCD proteins.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated beta (1,4)-galactosyltransferase I catalytic domain comprising SEQ ID NO: 5, wherein said catalytic domain catalyzes the formation of a glucose-beta(1,4)-N-acetylglucosamine bond at a greater rate than wild-type beta (1,4)-galactosyltransferase I catalytic domain, and wherein (a) the catalytic domain has a conservative amino acid exchange at amino acid position 228 of SEQ ID NO: 5, (b) the catalytic domain has a conservative amino acid exchange at amino acid position 229 of SEQ ID NO: 5, (c) the catalytic domain has conservative amino acid exchanges at amino acid positions 228 and 229 of SEQ ID NO: 5, (d) lysine is exchanged for arginine at amino acid position 228 of SEQ ID NO: 5, or (e) lysine is exchanged for arginine at amino acid position 228 and glycine is exchanged for alanine at amino acid position 229 of SEQ ID NO: 5, and wherein the rate of formation of the glucose-beta (1,4)-N-acetylglucosamine bond is at least two-fold greater, and wherein the wild-type .beta.(1,4)-galactosyltransferase I catalytic domain comprises FNRAKLL (SEQ ID NO: 1).

2. A kit comprising packaging material, and an isolated .beta.(1,4)-galactosyltransferase I catalytic domain comprising SEQ ID NO: 5 that: can catalyze formation of a glucose-.beta.(1,4)-N-acetylglucosamine bond at a greater rate than wild-type .beta.(1,4)-galactosyltransferase I and wherein (a) the catalytic domain has a conservative amino acid exchange at amino acid position 228 of SEQ ID NO: 5, (b) the catalytic domain has a conservative amino acid exchange at amino acid position 229 of SEQ ID NO: 5, (c) the catalytic domain has conservative amino acid exchanges at amino acid positions 228 and 229 of SEQ ID NO: 5, (d) lysine is exchanged for arginine at amino acid position 228 of SEQ ID NO: 5, or (e) lysine is exchanged for arginine at amino acid position 228 and glycine is exchanged for alanine at amino acid position 229 of SEQ ID NO: 5, and wherein the rate of formation of the glucose-beta (1,4)-N-acetylglucosamine bond is at least two-fold greater, and wherein the wild-type .beta.(1,4)-galactosyltransferase I catalytic domain comprises FNRAKLL (SEQ ID NO: 1).

3. An isolated beta (1,4)-galactosyltransferase I catalytic domain comprising SEQ ID NO: 5, wherein said catalytic domain catalyzes the formation of a glucose-beta(1,4)-N-acetylglucosamine bond at a greater rate than wild-type beta (1,4)-galactosyltransferase I catalytic domain, and wherein (a) the catalytic domain has a conservative amino acid exchange at amino acid position 228 of SEQ ID NO: 5, (b) the catalytic domain has a conservative amino acid exchange at amino acid position 229 of SEQ ID NO: 5, (c) the catalytic domain has conservative amino acid exchanges at amino acid positions 228 and 229 of SEQ ID NO: 5, (d) lysine is exchanged for arginine at amino acid position 228 of SEQ ID NO: 5, or (e) lysine is exchanged for arginine at amino acid position 228 and glycine is exchanged for alanine at amino acid position 229 of SEQ ID NO: 5, and wherein the rate of formation of the glucose-beta (1,4)-N-acetylglucosamine bond is at least at least five-fold greater, and wherein the wild-type .beta.(1,4)-galactosyltransferase I catalytic domain comprises FNRAKLL (SEQ ID NO: 1).

4. An isolated beta (1,4)-galactosyltransferase I catalytic domain comprising SEQ ID NO: 5, wherein said catalytic domain catalyzes the formation of a glucose-beta(1,4)-N-acetylglucosamine bond at a greater rate than wild-type beta (1,4)-galactosyltransferase I catalytic domain, and wherein (a) the catalytic domain has a conservative amino acid exchange at amino acid position 228 of SEQ ID NO: 5, (b) the catalytic domain has a conservative amino acid exchange at amino acid position 229 of SEQ ID NO: 5, (c) the catalytic domain has conservative amino acid exchanges at amino acid positions 228 and 229 of SEQ ID NO: 5, (d) lysine is exchanged for arginine at amino acid position 228 of SEQ ID NO: 5, or (e) lysine is exchanged for arginine at amino acid position 228 and glycine is exchanged for alanine at amino acid position 229 of SEQ ID NO: 5, and wherein the rate of formation of the glucose-beta (1,4)-N-acetylglucosamine bond is at least at least ten-fold greater, and wherein the wild-type .beta.(1,4)-galactosyltransferase I catalytic domain comprises FNRAKLL (SEQ ID NO: 1).

5. A kit comprising packaging material, and an isolated .beta.(1,4)-galactosyltransferase I catalytic domain comprising SEQ ID NO: 5 that: can catalyze formation of a glucose-.beta.(1,4)-N-acetylglucosamine bond at a greater rate than wild-type .beta.(1,4)-galactosyltransferase I and wherein (a) the catalytic domain has a conservative amino acid exchange at amino acid position 228 of SEQ ID NO: 5, (b) the catalytic domain has a conservative amino acid exchange at amino acid position 229 of SEQ ID NO: 5, (c) the catalytic domain has conservative amino acid exchanges at amino acid positions 228 and 229 of SEQ ID NO: 5, (d) lysine is exchanged for arginine at amino acid position 228 of SEQ ID NO: 5, or (e) lysine is exchanged for arginine at amino acid position 228 and glycine is exchanged for alanine at amino acid position 229 of SEQ ID NO: 5, and wherein the rate of formation of the glucose-beta (1,4)-N-acetylglucosamine bond is at least five-fold greater, and wherein the wild-type .beta.(1,4)-galactosyltransferase I catalytic domain comprises FNRAKLL (SEQ ID NO: 1).

6. A kit comprising packaging material, and an isolated .beta. (1,4)-galactosyltransferase I catalytic domain comprising SEQ ID NO: 5 that: can catalyze formation of a glucose-.beta.(1,4)-N-acetylglucosamine bond at a greater rate than wild-type .beta.(1,4)-galactosyltransferase I and wherein (a) the catalytic domain has a conservative amino acid exchange at amino acid position 228 of SEQ ID NO: 5, (b) the catalytic domain has a conservative amino acid exchange at amino acid position 229 of SEQ ID NO: 5, (c) the catalytic domain has conservative amino acid exchanges at amino acid positions 228 and 229 of SEQ ID NO: 5, (d) lysine is exchanged for arginine at amino acid position 228 of SEQ ID NO: 5, or (e) lysine is exchanged for arginine at amino acid position 228 and glycine is exchanged for alanine at amino acid position 229 of SEQ ID NO: 5, and wherein the rate of formation of the glucose-beta (1,4)-N-acetylglucosamine bond is at least ten-fold greater, and wherein the wild-type .beta.(1,4)-galactosyltransferase I catalytic domain comprises FNRAKLL (SEQ ID NO: 1).

7. The kit of an one of claims 2, or 5 or 6 further comprising a sugar nucleotide donor, wherein the donor is selected from the group consisting of: UDP-galactose, UDP-mannose, UDP-N-acetylglucosamine, UDP-glucose, UDP-N-acetylgalactosamine, and UDP-glucuronic acid.

* * * * *

SEQUENCE LISTING

<160> NUMBER OF SEQ ID NOS: 23

<210> SEQ ID NO 1
<211> LENGTH: 7
<212> TYPE: PRT
<213> ORGANISM: Homo sapiens

<400> SEQUENCE: 1

Phe Asn Arg Ala Lys Leu Leu
1               5

```
<210> SEQ ID NO 2
<211> LENGTH: 7
<212> TYPE: PRT
<213> ORGANISM: Homo sapiens

<400> SEQUENCE: 2

Tyr Val Gln Tyr Phe Gly Gly
1               5

<210> SEQ ID NO 3
<211> LENGTH: 398
<212> TYPE: PRT
<213> ORGANISM: Homo sapiens

<400> SEQUENCE: 3

Met Arg Leu Arg Glu Pro Leu Leu Ser Arg Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ile Gly Gln Ser Ser Gly Asp Leu Arg Thr Gly Gly
65                  70                  75                  80

Gly Ala Arg Pro Pro Pro Leu Gly Ala Ser Ser Gln Pro Arg Pro Gly
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Ser Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
305                 310                 315                 320
```

```
Leu Val Phe Arg Gly Met Ser Ile Ser Arg Pro Asn Ala Val Val Gly
                325                 330                 335

Thr Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395

<210> SEQ ID NO 4
<211> LENGTH: 399
<212> TYPE: PRT
<213> ORGANISM: Mus musculus

<400> SEQUENCE: 4

Met Arg Phe Arg Glu Gln Phe Leu Gly Gly Ser Ala Ala Met Pro Gly
 1               5                  10                  15

Ala Thr Leu Gln Arg Ala Cys Arg Leu Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Thr Leu Gln Gly Gly Thr
    50                  55                  60

Asn Gly Ala Ala Ala Ser Lys Gln Pro Pro Gly Glu Gln Arg Pro Arg
65                  70                  75                  80

Gly Ala Arg Pro Pro Pro Leu Gly Val Ser Pro Lys Pro Arg Pro
                85                  90                  95

Gly Leu Asp Ser Ser Pro Gly Ala Ala Ser Gly Pro Gly Leu Lys Ser
            100                 105                 110

Asn Leu Ser Ser Leu Pro Val Pro Thr Thr Gly Leu Leu Ser Leu
        115                 120                 125

Pro Ala Cys Pro Glu Glu Ser Pro Leu Leu Val Gly Pro Met Leu Ile
    130                 135                 140

Asp Phe Asn Ile Ala Val Asp Leu Glu Leu Leu Ala Lys Lys Asn Pro
145                 150                 155                 160

Glu Ile Lys Thr Gly Gly Arg Tyr Ser Pro Lys Asp Cys Val Ser Pro
                165                 170                 175

His Lys Val Ala Ile Ile Pro Phe Arg Asn Arg Gln Glu His Leu
            180                 185                 190

Lys Tyr Trp Leu Tyr Tyr Leu His Pro Ile Leu Gln Arg Gln Gln Leu
        195                 200                 205

Asp Tyr Gly Ile Tyr Val Ile Asn Gln Ala Gly Asp Thr Met Phe Asn
    210                 215                 220

Arg Ala Lys Leu Leu Asn Ile Gly Phe Gln Glu Ala Leu Lys Asp Tyr
225                 230                 235                 240

Asp Tyr Asn Cys Phe Val Phe Ser Asp Val Asp Leu Ile Pro Met Asp
                245                 250                 255

Asp Arg Asn Ala Tyr Arg Cys Phe Ser Gln Pro Arg His Ile Ser Val
            260                 265                 270

Ala Met Asp Lys Phe Gly Phe Ser Leu Pro Tyr Val Gln Tyr Phe Gly
        275                 280                 285

Gly Val Ser Ala Leu Ser Lys Gln Gln Phe Leu Ala Ile Asn Gly Phe
    290                 295                 300
```

```
Pro Asn Asn Tyr Trp Gly Trp Gly Gly Glu Asp Asp Ile Phe Asn
305                 310                 315                 320

Arg Leu Val His Lys Gly Met Ser Ile Ser Arg Pro Asn Ala Val Val
            325                 330                 335

Gly Arg Cys Arg Met Ile Arg His Ser Arg Asp Lys Lys Asn Glu Pro
            340                 345                 350

Asn Pro Gln Arg Phe Asp Arg Ile Ala His Thr Lys Glu Thr Met Arg
        355                 360                 365

Phe Asp Gly Leu Asn Ser Leu Thr Tyr Lys Val Leu Asp Val Gln Arg
370                 375                 380

Tyr Pro Leu Tyr Thr Gln Ile Thr Val Asp Ile Gly Thr Pro Arg
385                 390                 395
```

<210> SEQ ID NO 5
<211> LENGTH: 402
<212> TYPE: PRT
<213> ORGANISM: Bos taurus

<400> SEQUENCE: 5

```
Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
```

```
                275                 280                 285
Tyr Phe Gly Gly Val Ser Ala Leu Ser Lys Gln Gln Phe Leu Ser Ile
            290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 6
<211> LENGTH: 113
<212> TYPE: PRT
<213> ORGANISM: Homo sapiens

<400> SEQUENCE: 6

Arg Asp Leu Ser Arg Leu Pro Gln Leu Val Gly Val Ser Thr Pro Leu
1               5                   10                  15

Gln Gly Gly Ser Asn Ser Ala Ala Ile Gly Gln Ser Ser Gly Asp
            20                  25                  30

Leu Arg Thr Gly Gly Ala Arg Pro Pro Pro Leu Gly Ala Ser Ser
        35                  40                  45

Gln Pro Arg Pro Gly Gly Asp Ser Ser Pro Val Val Asp Ser Gly Pro
    50                  55                  60

Gly Pro Ala Ser Asn Leu Thr Ser Val Pro Val Pro His Thr Thr Ala
65                  70                  75                  80

Leu Ser Leu Pro Ala Cys Pro Glu Glu Ser Pro Leu Leu Val Gly Pro
                85                  90                  95

Met Leu Ile Glu Phe Asn Met Pro Val Asp Leu Glu Leu Val Ala Lys
            100                 105                 110

Gln

<210> SEQ ID NO 7
<211> LENGTH: 85
<212> TYPE: PRT
<213> ORGANISM: Bos taurus

<400> SEQUENCE: 7

Arg Asp Leu Arg Arg Leu Pro Gln Leu Val Gly Val His Pro Pro Leu
1               5                   10                  15

Gln Gly Ser Ser His Gly Ala Ala Ala Ile Gly Gln Pro Ser Gly Glu
            20                  25                  30

Leu Arg Leu Arg Gly Val Ala Pro Pro Pro Leu Gln Asn Ser Ser
        35                  40                  45

Lys Pro Arg Ser Arg Ala Pro Ser Asn Leu Asp Ala Tyr Ser His Pro
    50                  55                  60

Gly Pro Gly Pro Gly Pro Gly Ser Asn Leu Thr Ser Ala Pro Val Pro
65                  70                  75                  80
```

Ser Thr Thr Thr Arg
                85

<210> SEQ ID NO 8
<211> LENGTH: 273
<212> TYPE: PRT
<213> ORGANISM: Homo sapiens

<400> SEQUENCE: 8

Ser Leu Pro Ala Cys Pro Glu Glu Ser Pro Leu Val Gly Pro Met
  1               5                  10                  15

Leu Ile Glu Phe Asn Met Pro Val Asp Leu Glu Leu Val Ala Lys Gln
             20                  25                  30

Asn Pro Asn Val Lys Met Gly Gly Arg Tyr Ala Pro Arg Asp Cys Val
             35                  40                  45

Ser Pro His Lys Val Ala Ile Ile Pro Phe Arg Asn Arg Gln Glu
         50                  55                  60

His Leu Lys Tyr Trp Leu Tyr Tyr Leu His Pro Val Leu Gln Arg Gln
 65                  70                  75                  80

Gln Leu Asp Tyr Gly Ile Tyr Val Ile Asn Gln Ala Gly Asp Thr Ile
                 85                  90                  95

Phe Asn Arg Ala Lys Leu Leu Asn Val Gly Phe Gln Glu Ala Leu Lys
            100                 105                 110

Asp Tyr Asp Tyr Thr Cys Phe Val Phe Ser Asp Val Asp Leu Ile Pro
            115                 120                 125

Met Asn Asp His Asn Ala Tyr Arg Cys Phe Ser Gln Pro Arg His Ile
        130                 135                 140

Ser Val Ala Met Asp Lys Phe Gly Phe Ser Leu Pro Tyr Val Gln Tyr
145                 150                 155                 160

Phe Gly Gly Val Ser Ala Ser Ser Lys Gln Gln Phe Leu Thr Ile Asn
                165                 170                 175

Gly Phe Pro Asn Asn Tyr Trp Gly Trp Gly Gly Glu Asp Asp Asp Ile
            180                 185                 190

Phe Asn Arg Leu Val Phe Arg Gly Met Ser Ile Ser Arg Pro Asn Ala
        195                 200                 205

Val Val Gly Thr Cys Arg Met Ile Arg His Ser Arg Asp Lys Lys Asn
    210                 215                 220

Glu Pro Asn Pro Gln Arg Phe Asp Arg Ile Ala His Thr Lys Glu Thr
225                 230                 235                 240

Met Leu Ser Asp Gly Leu Asn Ser Leu Thr Tyr Gln Val Leu Asp Val
                245                 250                 255

Gln Arg Tyr Pro Leu Tyr Thr Gln Ile Thr Val Asp Ile Gly Thr Pro
            260                 265                 270

Ser

<210> SEQ ID NO 9
<211> LENGTH: 273
<212> TYPE: PRT
<213> ORGANISM: Bos taurus

<400> SEQUENCE: 9

Ser Leu Thr Ala Cys Pro Glu Glu Ser Pro Leu Val Gly Pro Met
  1               5                  10                  15

Leu Ile Glu Phe Asn Ile Pro Val Asp Leu Lys Leu Ile Glu Gln Gln
             20                  25                  30

Asn Pro Lys Val Lys Leu Gly Gly Arg Tyr Thr Pro Met Asp Cys Ile

```
                35                  40                  45
Ser Pro His Lys Val Ala Ile Ile Leu Phe Arg Asn Arg Gln Glu
     50                  55                  60

His Leu Lys Tyr Trp Leu Tyr Leu His Pro Met Val Gln Arg Gln
 65                  70                  75                  80

Gln Leu Asp Tyr Gly Ile Tyr Val Ile Asn Gln Ala Gly Glu Ser Met
                 85                  90                  95

Phe Asn Arg Ala Lys Leu Leu Asn Val Gly Phe Lys Glu Ala Leu Lys
             100                 105                 110

Asp Tyr Asp Tyr Asn Cys Phe Val Phe Ser Asp Val Asp Leu Ile Pro
         115                 120                 125

Met Asn Asp His Asn Thr Tyr Arg Cys Phe Ser Gln Pro Arg His Ile
    130                 135                 140

Ser Val Ala Met Asp Lys Phe Gly Phe Ser Leu Pro Tyr Val Gln Tyr
145                 150                 155                 160

Phe Gly Gly Val Ser Ala Leu Ser Lys Gln Gln Phe Leu Ser Ile Asn
                165                 170                 175

Gly Phe Pro Asn Asn Tyr Trp Gly Trp Gly Gly Glu Asp Asp Asp Ile
            180                 185                 190

Tyr Asn Arg Leu Ala Phe Arg Gly Met Ser Val Ser Arg Pro Asn Ala
        195                 200                 205

Val Ile Gly Lys Cys Arg Met Ile Arg His Ser Arg Asp Lys Lys Asn
    210                 215                 220

Glu Pro Asn Pro Gln Arg Phe Asp Arg Ile Ala His Thr Lys Glu Thr
225                 230                 235                 240

Met Leu Ser Asp Gly Leu Asn Ser Leu Thr Tyr Met Val Leu Glu Val
                245                 250                 255

Gln Arg Tyr Pro Leu Tyr Thr Lys Ile Thr Val Asp Ile Gly Thr Pro
            260                 265                 270

Ser

<210> SEQ ID NO 10
<211> LENGTH: 1197
<212> TYPE: PRT
<213> ORGANISM: Homo sapiens

<400> SEQUENCE: 10

Ala Thr Gly Ala Gly Gly Cys Thr Thr Cys Gly Gly Gly Ala Gly Cys
  1               5                  10                  15

Cys Gly Cys Thr Cys Cys Thr Gly Ala Gly Cys Cys Gly Gly Ala Gly
                 20                  25                  30

Cys Gly Cys Cys Gly Cys Gly Ala Thr Gly Cys Cys Ala Gly Gly Cys
            35                  40                  45

Gly Cys Gly Thr Cys Cys Thr Ala Cys Ala Gly Cys Gly Gly Gly Gly
        50                  55                  60

Cys Cys Thr Gly Cys Cys Gly Cys Cys Thr Gly Cys Thr Cys Gly Thr
 65                  70                  75                  80

Gly Gly Cys Cys Gly Thr Cys Thr Gly Cys Gly Cys Thr Cys Thr Gly
                 85                  90                  95

Cys Ala Cys Cys Thr Thr Gly Gly Cys Gly Thr Cys Ala Cys Cys Cys
            100                 105                 110

Thr Cys Gly Thr Thr Thr Ala Cys Thr Ala Cys Cys Thr Gly Gly Cys
        115                 120                 125

Thr Gly Gly Cys Cys Gly Cys Gly Ala Cys Cys Thr Gly Ala Gly Cys
```

```
            130                 135                 140
Cys Gly Cys Cys Thr Gly Cys Cys Cys Ala Ala Cys Thr Gly Gly
145                 150                 155                 160

Thr Cys Gly Gly Ala Gly Thr Cys Thr Cys Ala Cys Ala Cys Cys
                165                 170                 175

Gly Cys Thr Gly Cys Ala Gly Gly Cys Gly Gly Thr Cys Gly
                180                 185                 190

Ala Ala Cys Ala Gly Thr Gly Cys Gly Cys Cys Gly Cys Cys Ala
                195                 200                 205

Thr Cys Gly Gly Cys Ala Gly Thr Cys Thr Cys Cys Gly Gly
210                 215                 220

Gly Gly Ala Cys Cys Thr Cys Cys Gly Gly Ala Cys Cys Gly Gly Ala
225                 230                 235                 240

Gly Gly Gly Gly Cys Cys Cys Gly Gly Cys Cys Gly Cys Gly Cys
                245                 250                 255

Cys Thr Cys Cys Thr Cys Thr Ala Gly Gly Cys Gly Gly Cys Thr Cys
                260                 265                 270

Cys Thr Cys Cys Ala Gly Cys Cys Gly Gly Cys Cys Cys Gly
                275                 280                 285

Gly Gly Thr Gly Gly Cys Gly Ala Cys Thr Cys Cys Ala Gly Cys Cys
                290                 295                 300

Cys Ala Gly Thr Cys Gly Thr Gly Gly Ala Thr Thr Cys Thr Gly Gly
305                 310                 315                 320

Cys Cys Cys Thr Gly Gly Cys Cys Cys Gly Cys Thr Ala Gly Cys
                325                 330                 335

Ala Ala Cys Thr Thr Gly Ala Cys Cys Thr Cys Gly Gly Thr Cys Cys
                340                 345                 350

Cys Ala Gly Thr Gly Cys Cys Cys Ala Cys Ala Cys Cys Ala Cys
                355                 360                 365

Cys Gly Cys Ala Cys Thr Gly Thr Cys Gly Cys Thr Gly Cys Cys Cys
                370                 375                 380

Gly Cys Cys Thr Gly Cys Cys Cys Thr Gly Ala Gly Gly Ala Gly Thr
385                 390                 395                 400

Cys Cys Cys Cys Gly Cys Thr Gly Cys Thr Thr Gly Thr Gly Gly
                405                 410                 415

Cys Cys Cys Cys Ala Thr Gly Cys Thr Gly Ala Thr Gly Ala Gly
                420                 425                 430

Thr Thr Thr Ala Ala Cys Ala Thr Gly Cys Cys Thr Gly Thr Gly Gly
                435                 440                 445

Ala Cys Cys Thr Gly Gly Ala Gly Cys Thr Cys Gly Thr Gly Gly Cys
450                 455                 460

Ala Ala Ala Gly Cys Ala Gly Ala Cys Cys Cys Ala Ala Ala Thr
465                 470                 475                 480

Gly Thr Gly Ala Ala Gly Ala Thr Gly Gly Cys Gly Gly Cys
                485                 490                 495

Gly Cys Thr Ala Thr Gly Cys Cys Cys Cys Ala Gly Gly Gly Ala
                500                 505                 510

Cys Thr Gly Cys Gly Thr Cys Thr Cys Thr Cys Thr Cys Ala Cys
                515                 520                 525

Ala Ala Gly Gly Thr Gly Gly Cys Ala Thr Cys Ala Thr Cys Ala
                530                 535                 540

Thr Thr Cys Cys Ala Thr Thr Cys Cys Gly Cys Ala Ala Cys Cys Gly
545                 550                 555                 560
```

-continued

```
Gly Cys Ala Gly Gly Ala Gly Cys Ala Cys Cys Thr Cys Ala Ala Gly
                565                 570                 575

Thr Ala Cys Thr Gly Gly Cys Thr Ala Thr Ala Thr Thr Ala Thr Thr
            580                 585                 590

Thr Gly Cys Ala Cys Cys Cys Ala Gly Thr Cys Cys Thr Gly Cys Ala
        595                 600                 605

Gly Cys Gly Cys Cys Ala Gly Cys Ala Gly Cys Thr Gly Gly Ala Cys
    610                 615                 620

Thr Ala Thr Gly Gly Cys Ala Thr Cys Thr Ala Thr Gly Thr Thr Ala
625                 630                 635                 640

Thr Cys Ala Ala Cys Cys Ala Gly Gly Cys Gly Gly Gly Ala Gly Ala
                645                 650                 655

Cys Ala Cys Thr Ala Thr Ala Thr Thr Cys Ala Ala Thr Cys Gly Thr
            660                 665                 670

Gly Cys Thr Ala Ala Gly Cys Thr Cys Cys Thr Cys Ala Ala Thr Gly
        675                 680                 685

Thr Thr Gly Gly Cys Thr Thr Thr Cys Ala Ala Gly Ala Ala Gly Cys
    690                 695                 700

Cys Thr Thr Gly Ala Ala Gly Gly Ala Cys Thr Ala Thr Gly Ala Cys
705                 710                 715                 720
Thr Ala Cys Ala Cys Cys Thr Gly Cys Thr Thr Thr Gly Thr Gly Thr
                725                 730                 735
Thr Thr Ala Gly Thr Gly Ala Cys Gly Thr Gly Gly Ala Cys Cys Thr
            740                 745                 750

Cys Ala Thr Thr Cys Cys Ala Ala Thr Gly Ala Ala Thr Gly Ala Thr
        755                 760                 765

Cys Ala Thr Ala Ala Thr Gly Cys Gly Thr Ala Cys Ala Gly Gly Thr
    770                 775                 780

Gly Thr Thr Thr Thr Thr Cys Ala Cys Ala Gly Cys Cys Ala Cys Gly
785                 790                 795                 800

Gly Cys Ala Cys Ala Thr Thr Thr Cys Cys Gly Thr Thr Gly Cys Ala
                805                 810                 815

Ala Thr Gly Gly Ala Thr Ala Ala Gly Thr Thr Thr Gly Gly Ala Thr
            820                 825                 830

Thr Cys Ala Gly Cys Cys Thr Ala Cys Cys Thr Thr Ala Thr Gly Thr
        835                 840                 845

Thr Cys Ala Gly Thr Ala Thr Thr Thr Thr Gly Gly Ala Gly Gly Thr
    850                 855                 860

Gly Thr Cys Thr Cys Thr Gly Cys Thr Thr Cys Ala Ala Gly Thr Ala
865                 870                 875                 880

Ala Ala Cys Ala Ala Cys Ala Gly Thr Thr Thr Cys Thr Ala Ala Cys
                885                 890                 895

Cys Ala Thr Cys Ala Ala Thr Gly Gly Ala Thr Thr Thr Cys Cys Thr
            900                 905                 910

Ala Ala Thr Ala Ala Thr Thr Ala Thr Thr Gly Gly Gly Gly Cys Thr
        915                 920                 925

Gly Gly Gly Gly Ala Gly Gly Ala Gly Ala Ala Gly Ala Thr Gly Ala
    930                 935                 940

Thr Gly Ala Cys Ala Thr Thr Thr Thr Thr Ala Ala Cys Ala Gly Ala
945                 950                 955                 960

Thr Thr Ala Gly Thr Thr Thr Thr Thr Ala Gly Ala Gly Gly Cys Ala
                965                 970                 975
```

```
Thr Gly Thr Cys Thr Ala Thr Ala Cys Thr Cys Gly Cys Cys
            980                 985                 990

Ala Ala Ala Thr Gly Cys Thr Gly Thr Gly Thr Cys Gly Gly Gly
        995                1000                1005

Ala Cys Gly Thr Gly Thr Cys Gly Cys Ala Thr Gly Ala Thr Cys
        1010               1015                1020

Gly Cys Cys Ala Cys Thr Cys Ala Ala Gly Gly Ala Cys Ala Ala
1025                1030                1035                1040

Gly Ala Ala Ala Ala Ala Thr Gly Ala Ala Cys Cys Ala Ala Thr
            1045                1050                1055

Cys Cys Thr Cys Ala Gly Ala Gly Gly Thr Thr Thr Gly Ala Cys Cys
            1060                1065                1070

Gly Ala Ala Thr Thr Gly Cys Ala Cys Ala Cys Ala Cys Ala Ala Ala
            1075                1080                1085

Gly Gly Ala Gly Ala Cys Ala Ala Thr Gly Cys Thr Cys Thr Cys Thr
1090                1095                1100

Gly Ala Thr Gly Gly Thr Thr Thr Gly Ala Ala Cys Thr Cys Ala Cys
1105                1110                1115                1120

Thr Cys Ala Cys Cys Thr Ala Cys Cys Ala Gly Gly Thr Gly Cys Thr
            1125                1130                1135

Gly Gly Ala Thr Gly Thr Ala Cys Ala Gly Ala Gly Ala Thr Ala Cys
            1140                1145                1150

Cys Cys Ala Thr Thr Gly Thr Ala Thr Ala Cys Cys Ala Ala Ala
            1155                1160                1165

Thr Cys Ala Cys Ala Gly Thr Gly Gly Ala Cys Ala Thr Cys Gly Gly
            1170                1175                1180

Gly Ala Cys Ala Cys Cys Gly Ala Gly Cys Thr Ala Gly
1185                1190                1195

<210> SEQ ID NO 11
<211> LENGTH: 42
<212> TYPE: DNA
<213> ORGANISM: Artificial Sequence
<220> FEATURE:
<223> OTHER INFORMATION: A synthetic primer

<400> SEQUENCE: 11
ccttacgtgc aattgtttgg aggtgtctct gctctaagta aa              42

<210> SEQ ID NO 12
<211> LENGTH: 36
<212> TYPE: DNA
<213> ORGANISM: Artificial Sequence
<220> FEATURE:
<223> OTHER INFORMATION: A synthetic primer

<400> SEQUENCE: 12
gacacctcca acaattgca cgtaaggtag gctaaa                      36

<210> SEQ ID NO 13
<211> LENGTH: 41
<212> TYPE: DNA
<213> ORGANISM: Artificial Sequence
<220> FEATURE:
<223> OTHER INFORMATION: A synthetic primer

<400> SEQUENCE: 13
ctaccttacg tgcagatctt tggaggtgtc tctgctctaa g               41
```

<210> SEQ ID NO 14
<211> LENGTH: 40
<212> TYPE: DNA
<213> ORGANISM: Artificial Sequence
<220> FEATURE:
<223> OTHER INFORMATION: A synthetic primer

<400> SEQUENCE: 14
gacacctcca aagatctgca cgtaaggtag gctaatccaa                                40

<210> SEQ ID NO 15
<211> LENGTH: 41
<212> TYPE: DNA
<213> ORGANISM: Artificial Sequence
<220> FEATURE:
<223> OTHER INFORMATION: A synthetic primer

<400> SEQUENCE: 15
ggattagcct accatatgtg cagaattttg gaggtgtctc t                              41

<210> SEQ ID NO 16
<211> LENGTH: 42
<212> TYPE: DNA
<213> ORGANISM: Artificial Sequence
<220> FEATURE:
<223> OTHER INFORMATION: A synthetic primer

<400> SEQUENCE: 16
agagacacct ccaaaattct gcacatctgg taggctaaat cc                             42

<210> SEQ ID NO 17
<211> LENGTH: 39
<212> TYPE: DNA
<213> ORGANISM: Artificial Sequence
<220> FEATURE:
<223> OTHER INFORMATION: A synthetic primer

<400> SEQUENCE: 17
cgcggatccc gcgacctaag acgcctgcct cagctggtc                                 39

<210> SEQ ID NO 18
<211> LENGTH: 38
<212> TYPE: DNA
<213> ORGANISM: Artificial Sequence
<220> FEATURE:
<223> OTHER INFORMATION: A synthetic primer

<400> SEQUENCE: 18
tggaattcct agctcggcgt cccgatgtcc actgtgat                                  38

<210> SEQ ID NO 19
<211> LENGTH: 39
<212> TYPE: DNA
<213> ORGANISM: Homo sapiens

<400> SEQUENCE: 19
cgcggatccc gcgacctgag ccgcctgccc caactggtc                                 39

<210> SEQ ID NO 20
<211> LENGTH: 39
<212> TYPE: DNA
<213> ORGANISM: Homo sapiens

<400> SEQUENCE: 20
ccggaattcc tactagctcg gtgtcccgat gtccactgt                                 39

```
<210> SEQ ID NO 21
<211> LENGTH: 8
<212> TYPE: PRT
<213> ORGANISM: Bos taurus

<400> SEQUENCE: 21

Ser Arg Ala Pro Ser Asn Leu Asp
 1               5

<210> SEQ ID NO 22
<211> LENGTH: 11
<212> TYPE: PRT
<213> ORGANISM: Bos taurus

<400> SEQUENCE: 22

Lys Pro Arg Ser Arg Ala Pro Ser Asn Leu Asp
 1               5                  10

<210> SEQ ID NO 23
<211> LENGTH: 10
<212> TYPE: PRT
<213> ORGANISM: Homo sapiens

<400> SEQUENCE: 23

Gln Leu Val Gly Val Ser Thr Pro Leu Gln
 1               5                  10
```